US009241996B2

(12) United States Patent
Høgset et al.

(10) Patent No.: US 9,241,996 B2
(45) Date of Patent: Jan. 26, 2016

(54) PHOTOCHEMICAL INTERNALISATION OF KINASE INHIBITORS

(75) Inventors: Anders Høgset, Oslo (NO); Anette Weyergang, Oslo (NO); Pål Kristian Selbo, Oslo (NO); Kristian Berg, Heggedal (NO)

(73) Assignee: PCI BIOTECH AS, Oslo (NO)

( * ) Notice: Subject to any disclaimer, the term of this patent is extended or adjusted under 35 U.S.C. 154(b) by 935 days.

(21) Appl. No.: 13/001,750

(22) PCT Filed: Jun. 26, 2009

(86) PCT No.: PCT/GB2009/001618
§ 371 (c)(1),
(2), (4) Date: Aug. 19, 2011

(87) PCT Pub. No.: WO2010/001102
PCT Pub. Date: Jan. 7, 2010

(65) Prior Publication Data
US 2011/0293575 A1  Dec. 1, 2011

(30) Foreign Application Priority Data
Jun. 30, 2008  (GB) .................................. 0811955.4

(51) Int. Cl.
| | |
|---|---|
| A01N 63/02 | (2006.01) |
| A01N 63/00 | (2006.01) |
| C12N 5/071 | (2010.01) |
| C12N 5/02 | (2006.01) |
| A61K 31/50 | (2006.01) |
| A61K 31/4965 | (2006.01) |
| A61K 31/517 | (2006.01) |
| A01N 43/38 | (2006.01) |
| A61K 31/40 | (2006.01) |
| A61K 41/00 | (2006.01) |
| A61K 31/00 | (2006.01) |
| A61K 31/501 | (2006.01) |
| A01N 43/90 | (2006.01) |
| A01N 43/54 | (2006.01) |
| A61K 31/505 | (2006.01) |
| A01N 43/42 | (2006.01) |
| A61K 31/445 | (2006.01) |
| A01N 43/40 | (2006.01) |

(52) U.S. Cl.
CPC ............. *A61K 41/0071* (2013.01); *A61K 31/00* (2013.01)

(58) Field of Classification Search
USPC ............ 424/93.7; 435/325, 375; 514/252.18, 514/252.19, 253.06, 263.4, 266.4, 275, 291, 514/318, 320, 350, 414
See application file for complete search history.

(56) References Cited

U.S. PATENT DOCUMENTS

2007/0072933 A1   3/2007  Peyman
2010/0256136 A1 * 10/2010  Pandey et al. .............. 514/234.5

FOREIGN PATENT DOCUMENTS

| FR | 2867189 | | 9/2005 |
|---|---|---|---|
| FR | 2867189 | A1 * | 9/2005 |
| WO | 96/07432 | | 3/1996 |
| WO | 00/54802 | | 9/2000 |
| WO | 01/74389 | | 10/2001 |
| WO | 02/44396 | | 6/2002 |
| WO | 02/058730 | | 8/2002 |
| WO | 03/020309 | | 3/2003 |
| WO | 2004/041164 | | 5/2004 |
| WO | 2008/008215 | | 1/2008 |

OTHER PUBLICATIONS

Zhou et al. 2005. Enhancing the therapeutic responsiveness of photodynamic therapy with the anti-angiogenic agents SU5416 and SU6668 in murine nasopharyngeal carcinoma models. Cancer Chemotherapy and Pharmacology, vol. 56, pp. 569-577.*
Houghton et al. 2004. Imatinib Mesylate Is a Potent Inhibitor of the ABCG2 (BCRP) Transporter and Reverses Resistance to Topotecan and SN-38 in Vitro. vol. 64, pp. 2333-2337.*
Abbott et al. 2003. ABCG2 (BCRP) Expression in Normal and Malignant Hematopoietic Cells. Hematol Oncology, vol. 21, pp. 115-130.*
Berg, K. et al., Lysosomes and Microtubules as Targets for Photochemotherapy of Cancer, Photochemistry and Photobiology, 1997, 65(3): 403-409.
Robey, R. et al., ABCG2-Mediated Transport of Photosensitizers, Cancer Biology & Therapy, 2005, 4:2, 187-194.
Curiel, D., Strategies to Adapt Adenoviral Vectors for Targeted Delivery, Annals New York Acad. Sci., 1999, 886:158-171.
Bilbao, G. et al., Targeted Adenoviral Vectors For Cancer Gene Therapy, Gene Therapy of Cancer, edited by Walden et al., Plenum Press, New York, 1998.

(Continued)

*Primary Examiner* — Debbie K Ware
*Assistant Examiner* — Kailash C Srivastava
(74) *Attorney, Agent, or Firm* — Wenderoth, Lind & Ponack, L.L.P.

(57) ABSTRACT

The present invention relates to a method for enhancing the activity of kinase inhibitors in target cells, and more specifically for enhancing the activity of tyrosine kinase inhibitors (TKIs), said method comprising contacting a cell with a kinase inhibitor and a photosensitizing agent and irradiating said cell with light of a wavelength effective to activate the photosensitizing agent, and to the use of this method for enhancing the effects of kinase inhibitors or kinase inhibitor-based drugs in particular to achieve cell death, for example, in cancer treatment and other diseases or conditions in which kinase inhibitors, such as TKIs, have a beneficial effect.

27 Claims, 10 Drawing Sheets

(56) References Cited

OTHER PUBLICATIONS

Figure 1:
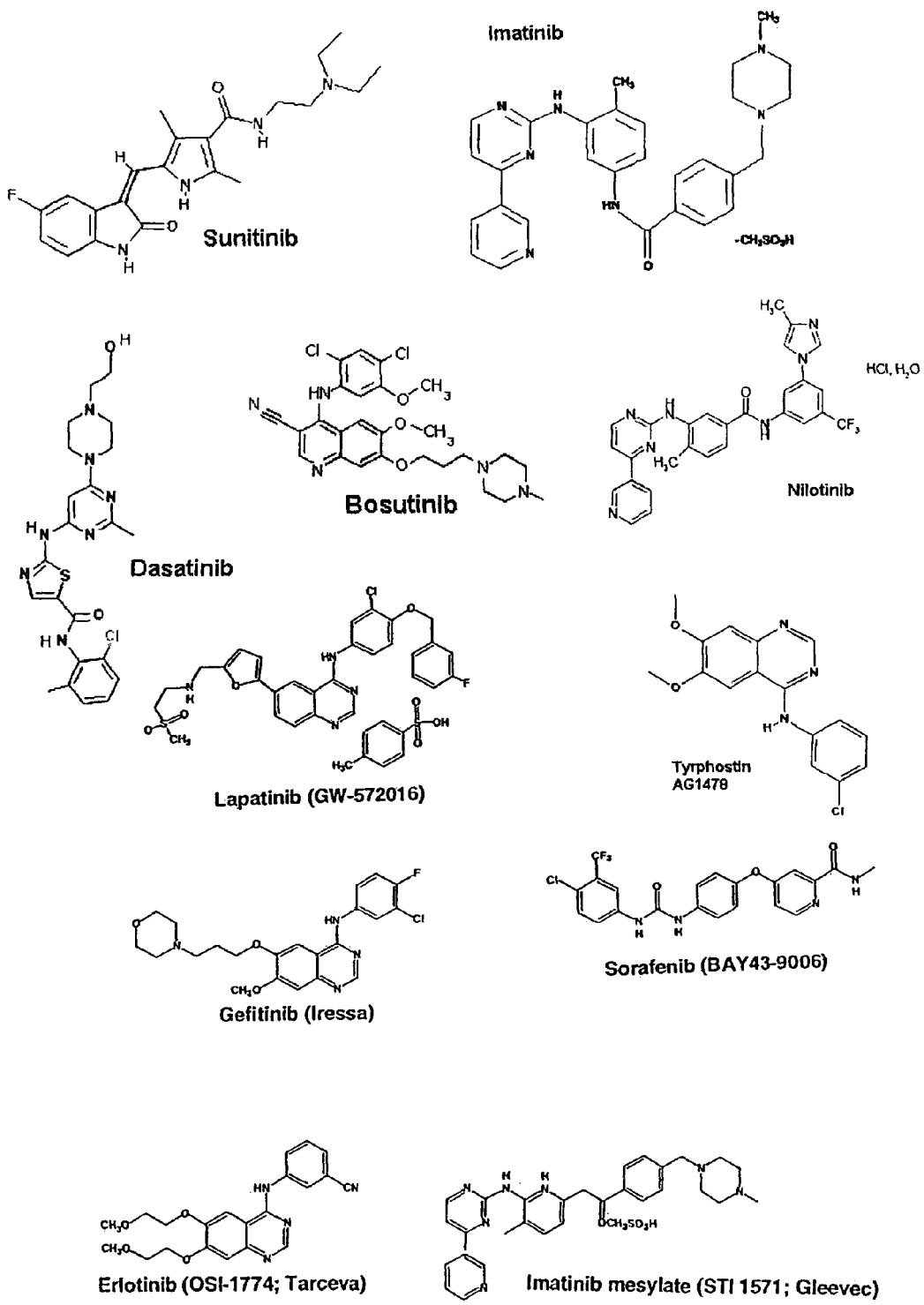
Figure 1:
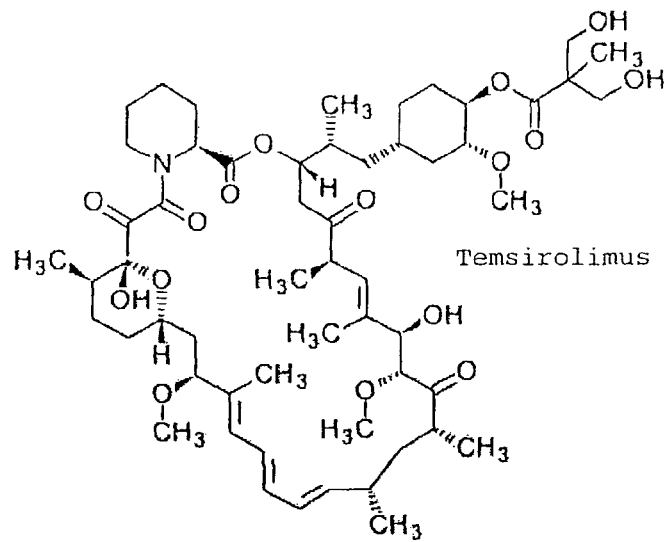
Figure 1:
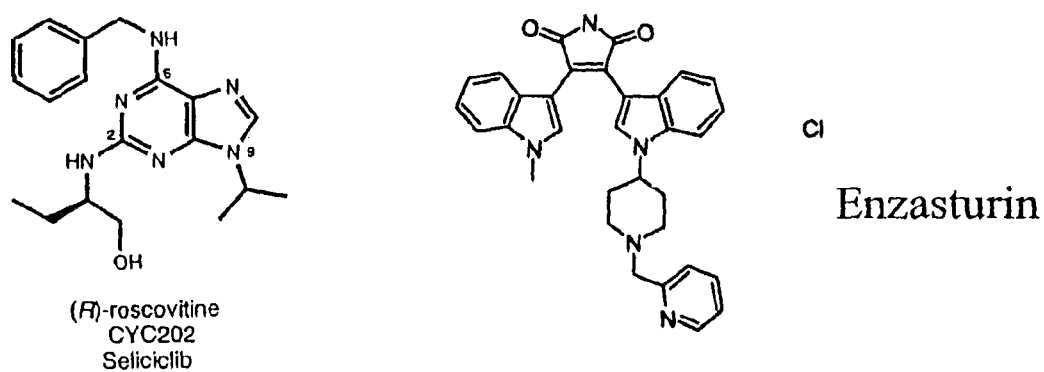
Figure 1:
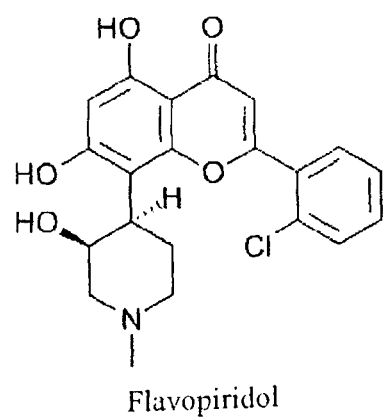

Peng, K.W. et al., Viral vector targeting, Current Opinion in Biotechnology 1999, 10:454-457.
Wickham, T.J., Targeting adenovirus, Gene Therapy (2000) 7, 110-114.
Weyergang, A. et al., Y1068 phosphorylation is the most sensitive target of disulfonated tetraphenylporphyrin-based photodynamic therapy on epidermal growth factor receptor, Biochemical Pharmacology 74 (2007) 226-235.
Sazani, P. et al., Nuclear antisense effects of neutral, anionic and cationic oligonucleotide analogs, Nucleic Acids Research (2001) 29(19):3965-3974.
Gomer, C. et al., Photodynamic Therapy-mediated Oxidative Stress Can Induce Expression of Heat Shock Proteins, Cancer Research (1996) 56:2355-2360.
Agrawal, A. et al., Overview of tyrosine kinase inhibitors in clinical breast cancer, Endocrine-Related Cancer (2005) 12:S135-S144.
Abu-Ali, S. et al., Tyrosine-kinase inhibition results in EGFR clustering at focal adhesions and consequent exocytosis in uPAR down-regulated cells of head and neck cancers, Molecular Cancer (2008) 7:47.
Weyergang A. et al., Photochemically stimulated drug delivery increases the cytotoxicity and specificity of EGF-saporin, Journal of Controlled Release (2006) 111:165-173.
Ahmad et al., In vitro and in vivo inhibition of epidermal growth factor receptor-tyrosine kinase pathway by photodynamic therapy, Oncogene (2001) 20, 2314-2317.
Del Carmen, M. et al., Synergism of Epidermal Growth Factor Receptor—Targeted Immunotherapy With Photodynamic Treatment of Ovarian Cancer In Vivo, Journal of the National Cancer Institute (2005) 97(20): 1516-1524.
International Search Report and Written Opinion for PCT/GB2009/001618, dated Aug. 2, 2010.
Liu, W. et al., The Tyrosine Kinase Inhibitor Imatinib Mesylate Enhances the Efficacy of Photodynamic Therapy by Inhibiting ABCG2., Clinical Cancer Research (2006) 13(8):2463-2470.
Thomas, J. et al., Active transport of imatinib into and out of cells: implications for drug resistance, Blood (2004) 104 (12):3739-3745.
White, D. et al., OCT-1—mediated influx is a key determinant of the intracellular uptake of imatinib but not nilotinib (AMN107): reduced OCT-1 activity is the cause of low in vitro sensitivity to imatinib, Blood (2006) 108(2):697-704.
Zhou, Q. et al., Enhancing the therapeutic responsiveness of photodynamic therapy with the antiangiogenic agents SU5416 and SU6668 in murine nasopharyngeal carcinoma models, Cancer Chemotherapy and Pharmacology (2005) 56:569-577.
Briggs, C. et al., The Effect of Combination Treatment with Gemcitabine and the EGFR-Receptor Tyrosine Kinase Inhibitor IRESSA with Photodynamic Therapy in Bladder Cancer, European Urology Supplements (2003) 2-44.
Weyergang, A. et al., Photodynamic targeting of EGFR does not predict the treatment outcome in combination with the EGFR tyrosine kinase inhibitor Tyrphostin AG1478, Photochem. Photobio. Sciences (2008) 7:1032-1030.
Weyergang, A. et al., Photodynamic Therapy Targets the rnTOR Signaling Network in Vitro and in Vivo, Molecular Pharmaceutics (2009) 6(1):255-264.
Selbo, P. et al., Photochemical Internalisation: A Novel Drug Delivery System, Tumor Biology (2002) 23:103-112.
Dimitroff, C. et al., Anti-angiogenic activity of selected receptor tyrosine kinase inhibitors, PD166285 and PD173074: Implications for combination treatment with photodynamic therapy, Investigational New Drugs (1999) 17(2):121-135.

* cited by examiner

PHOTOCHEMICAL INTERNALISATION OF KINASE INHIBITORS

METHOD

The present invention relates to a method for enhancing the activity of kinase inhibitors in target cells, and more specifically for enhancing the activity of tyrosine kinase inhibitors (TKIs), using a photosensitizing agent and irradiation of the cells with light of a wavelength effective to activate the photosensitizing agent, and to the use of this method for enhancing the effects of kinase inhibitors or kinase inhibitor-based drugs in particular to achieve cell death, for example, in cancer treatment and other diseases or conditions in which kinase inhibitors, such as TKIs, have a beneficial effect.

Protein kinases act by chemically adding phosphate groups to other proteins thereby achieving phosphorylation. The action of the kinase involves the removal of a phosphate group from ATP and attachment to one of three possible amino acids that have a free hydroxyl group, namely serine, threonine or tyrosine.

Such phosphorylation usually affects the functional properties of the target protein, by, for example, changing its activity or association with other proteins. Kinases are known to be heavily involved in regulation in the majority of cellular pathways, particularly in signal transduction. In view of their involvement in such pathways, deregulation of kinase activity is a frequent cause of disease, particularly cancer. As a consequence, drugs which inhibit specific kinases continue to be developed to treat various diseases.

Regulation of kinases may be achieved by binding of activators or inhibitors.

Serine/threonine protein kinases (EC 2.7.11.1) phosphorylate the hydroxy group of serine or threonine. Activity of these protein kinases can be regulated by specific events (e.g. DNA damage), as well as numerous chemical signals, including cAMP/cGMP, Diacylglycerol, and $Ca^{2+}$/calmodulin. Examples of this group of kinases are the MAP kinases (mitogen/microtubule-activated protein kinases). Important subgroups are the kinases of the ERK family, which are often activated by mitogenic signals, and stress-activated protein kinases (JNK, p38), which are activated by signals that include intracellular stress. While MAP kinases are serine/threonine-specific, they are activated by combined phosphorylation on serine/threonine and tyrosine residues.

Tyrosine-specific protein kinases (EC 2.7.10.1) phosphorylate tyrosine amino acid residues. They act primarily as growth factor receptors and in downstream signalling from growth factors. Examples include the epidermal growth factor receptor (EGFR), platelet-derived growth factor receptor (PDGFR) and insulin and insulin-like growth factor receptor (IGF1R).

Tyrosine kinases mediate signal transduction and propagation of a multitude of intra- and extra-cellular signals. In general, there are two types of protein tyrosine kinases. The first type of protein tyrosine kinases are receptor tyrosine kinases which have an extracellular ligand binding domain and an intracellular catalytic domain which has intrinsic tyrosine kinase activity. These kinases are characterised by immunoglobulin-like sequences in their amino terminal extracellular domain, a lipophilic transmembrane segment and intracellular carboxy-terminal domain that includes the tyrosine kinase catalytic site.

When a ligand binds to such a receptor it induces dimerisation of the receptor and autophosphorylation of the cytoplasmic domains and activation of tyrosine kinase activity. A range of downstream events result which include the possibility of further tyrosine kinases being stimulated. Other downstream effects include increased intracellular calcium levels, activation of serine/threonine kinases, phospholipase C and phosphatidylinositol-3'-kinase and changes in gene expression. Many tyrosine kinase substrates contain a Src homology 2 (SH2) domain which binds to phosphorylated tyrosine residues and mediates interaction of activated protein tyrosine kinases with substrates.

The second type of protein tyrosine kinases are receptor-associated tyrosine kinases which reside in the cell cytoplasm and interact with the cytoplasmic domains of membrane proteins and transmit signals from the cell membrane and relay the signal intracellularly. Examples include Janus kinase (JAK).

Some kinases have mixed kinase activities. For example, MEK (MAPKK), which is involved in the MAP kinase cascade, is a mixed serine/threonine and tyrosine kinase.

Kinases are an important therapeutic target in view of their importance in cell signalling. In particular, mutations in tyrosine kinases can lead to over-activation of the enzyme, which can lead to inappropriate cell growth. This may have pathological implications, for example resulting in tumour growth. In this regard, tyrosine kinase inhibitors (TKIs) are currently used therapeutically, for example in the treatment of cancer. TKIs are utilised on the premise that inhibition of cell signals that result in inappropriate growth of cells will be beneficial in the treatment of cancer.

Two classes of small molecule tyrosine kinase inhibitors currently exist, the first of which acts by binding to the ATP binding site and the other by binding to the substrate binding site of the enzyme.

Some examples of small molecule TKIs include: BCR-ABL inhibitors, for example Imatinib mesylate which inhibits both the ABL and BCR-ABL tyrosine kinases and which is used in the treatment of chronic myeloid leukemia; EGFR inhibitors, for example Gefitinib which inhibits ErbB1 and which is approved for treatment of patients with non-small cell lung cancer after failure of both platinum-based or docetaxel chemotherapies; Erlotinib hydrochloride, which is a selective inhibitor of ErbB1 tyrosine kinase; Lapatinib which is a reversible and specific receptor tyrosine kinase of both ErbB1 and ErbB2 and Canertinib which is an irreversible non-selective EGFR inhibitor. Other examples of small molecule TKIs include Tyrphostin (AG1478), Bosutinib and Nilotinib. These TKIs are merely examples of the many TKIs that are available today.

Serine/threonine kinase inhibitors are also used therapeutically. For example, the inhibitor Temsirolimus (trade name Torisel) is currently in use for treating renal cancer. This inhibitor is thought to indirectly inhibit the mTOR serine/threonine kinase. Other serine/threonine kinase inhibitors are undergoing various phases of clinical trials, for example, Enzastaurin for cancer treatment, Flavopirodol (a CDK4 inhibitor) for non-small cell lung cancer and CYC202 (R-roscovitine/Seliciclib, Cyclacel) for leukaemia, breast, colon and lung cancer. In addition, several Aurora kinase inhibitors are under development by different companies.

For many of the TKIs in use today development of resistance is a major problem, in many cases severely limiting the duration of the therapeutic effect. Furthermore, not all patients respond to therapy with a particular TKI. For example, leukemia patients have variable sensitivity to imatinib. In addition, any methods that would allow targetting of inhibitors to appropriate cells and/or increase their efficacy allowing lower doses or levels of the inhibitors to be used, are clearly desirable particularly in medical treatments in view of the potential reduction in systemic side effects in patients due to the inhibitors. For example, serious side effects associated with administration of Erlotinib have been reported.

The present invention serves to address this problem by providing a method to enhance the efficacy of kinase inhibitor action on cells, particularly in medical treatments. Thus, the overall aim of the improved method herein can be stated as a desire to enhance or improve the effect of kinase inhibitors and kinase inhibitor-based drugs, particularly TKIs.

In order to achieve this aim the inventors have combined the use of kinase inhibitors with photochemical treatment, particularly the techniques of photochemical internalisation (PCI) and/or photodynamic therapy (PDT).

The use of these techniques has been found to significantly improve the efficacy of the kinase inhibitor's action. The basis of this improvement is not yet known and is very surprising. As discussed below, PCI is principally known for release of internalized molecules from intracellular compartments such as endosomes. However, the effect has been observed with kinase inhibitors that are not expected to localise in endocytic vesicles and thus release from these compartments may not account for the improvements observed. It has however surprisingly been found that the photochemical treatment produces enhanced inhibitor effects, in particular synergy with the effects attributed to use of the kinase inhibitors alone has been observed. This synergy is dependent on exposure of the cell to a photosensitizing compound and subsequent irradiation, and as such, the kinase inhibitor effects can be controlled in a spatial or temporal manner.

This enhanced kinase effect also allows improved therapy e.g. in resistant patients, and the use of lower doses of the active ingredient. Thus, the improved efficacy of the kinase inhibitors allows an amount of inhibitor to be used which is not therapeutically effective when administered alone, i.e. without photochemical treatment. This means that lower doses of inhibitor can be used which may result in reduced side effects in the patient. By appropriate selection of the photosensitizer, PCI/PDT effects can be localized to target cells by virtue of selective uptake of the photosensitizer into diseased cells and in view of activation by irradiation of the photosensitizer which can be directed to only target cells, targetted selection of cells of interest can be achieved. Furthermore, the timing of activation by the PCI/PDT method can be controlled by initiation of the irradiation step of the method.

PCI is a technique which uses a photosensitizing agent, in combination with an irradiation step to activate that agent, and is known to achieve release of molecules co-administered to the cell into the cell's cytosol. This technique allows molecules that are taken up by the cell into organelles, such as endosomes, to be released from these organelles into the cytosol, following irradiation.

The basic method of photochemical internalisation (PCI), is described in WO 96/07432 and WO 00/54802, which are incorporated herein by reference. As set out above, the molecule to be internalised (which for use according to the present invention would be the kinase inhibitor), and a photosensitizing agent are brought into contact with a cell. The photosensitizing agent and the molecule to be internalised are taken up into a cellular membrane-bound subcompartment within the cell. On exposure of the cell to light of the appropriate wavelength, the photosensitizing agent is activated which directly or indirectly generates toxic species which disrupt the intracellular compartment membranes. This allows the internalized molecule to be released into the cytosol.

These methods use the photochemical effect as a mechanism for introducing otherwise membrane-impermeable molecules into the cytosol of a cell in a manner which does not result in widespread cell destruction or cell death if the methodology is suitably adjusted to avoid excessive toxic species production, e.g. by lowering illumination times or photosensitizer dose.

However, as mentioned above, it is not known if the enhanced kinase inhibitor activity observed after using the photochemical methods described herein results from release of the inhibitor from compartments into which it has been taken up within the cell. The terminology "PCI" has however been used herein to describe a methodology in which a photosensitizing agent is contacted with a cell and subjected to irradiation thereby activating that agent and in addition, before, during or after said irradiation the cell is also contacted with a kinase inhibitor which is taken up into the cell.

To achieve cell death by PCI, the agent which is taken up, or whose activity is enhanced according to the present invention, has cell killing properties, e.g. is a toxin, or in the present case is a kinase inhibitor whose activity leads to cell death. Where appropriate, when cell death is desired, the activation of the photosensitizer may be used to contribute to cell death, i.e. by using a PDT effect, discussed below.

PDT (photodynamic therapy) similarly uses photosensitizers that absorb energy from visible light and transform this energy to molecular oxygen creating reactive oxygen species (ROSs). Unlike PCI however, the level of the photochemically generated ROSs is sufficiently high (e.g. by the use of high concentrations of the photosensitizer or longer irradiation times) such that cells in which the ROSs are generated suffer cell death by apoptosis or necrosis. ROSs have short lifetimes, less than 40 ns for singlet oxygen ($^1O_2$) in biological systems and the photochemical reaction generated during PDT is therefore located in the direct vicinity of the photosensitizer. The intracellular targets of PDT are, as a result, highly dependent on the physio-chemical properties and the intracellular localisation of the photosensitizer at the time of light exposure.

PDT may be used in conjunction with a second agent, to aid cell death, e.g. in cells that are not killed by the PDT method. In those cells a PCI effect may take place, i.e. the second agent may be internalized in the cell or its activity enhanced such that in those cells that second agent causes cell death, e.g. by use of a TKI.

Thus, if cell death is desired according to the invention, a first alternative is to use a PCI method in which some cell death may occur from the generated ROSs (though this is likely to be minimal) but principally cell death occurs by virtue of the activity of the kinase inhibitor. In a second alternative a PDT-type method may be used in which a significant proportion of the cell death occurs from the generated ROSs though this is supplemented by cell death due to the kinase inhibitor which acts in cells which are not killed by the PDT method, i.e. in those cells a PCI-type method occurs.

PDT has been used for the treatment of cancers, however cancerous cells can become resistant to PDT. PCI, in which toxic molecules are internalized, has similarly been advocated for this purpose (see WO96/07432).

Thus, in a first aspect, the invention provides a method for enhancing the activity of a kinase inhibitor, preferably a tyrosine kinase inhibitor, comprising contacting a cell with said kinase inhibitor and a photosensitizing agent, and irradiating the cell with light of a wavelength effective to activate the photosensitizing agent.

The term "cell" is used herein to include all eukaryotic cells (including insect cells and fungal cells). Representative "cells" thus include all types of mammalian and non-mammalian animal cells, plant cells, insect cells, fungal cells and protozoa. Preferably however the cells are mammalian, for example cells from cats, dogs, horses, donkeys, sheep, pigs, goats, cows, mice, rats, rabbits, guinea pigs, but most preferably from humans.

As used herein "contacting" refers to bringing the cells and the photosensitizing agent and/or kinase inhibitor into physical contact with one another under conditions appropriate for internalization into the cells, e.g. preferably at 37° C. in an appropriate nutritional medium, e.g. from 25-39° C.

The photosensitizing agent is an agent which is activated on illumination at an appropriate wavelength and intensity to generate an activated species. Conveniently such an agent may be one which localises to intracellular compartments, particularly endosomes or lysosomes. A range of such photosensitizing agents are known in the art and are described in the literature, including in WO96/07432, which is incorporated herein by reference. Mention may be made in this respect of di- and tetrasulfonated aluminium phthalocyanine (e.g. $AlPcS_{2a}$), sulfonated tetraphenylporphines ($TPPS_n$), sulfonated tetraphenyl bacteriochlorins (e.g. $TPBS_{2a}$), nile blue, chlorin $e_6$ derivatives, uroporphyrin I, phylloerythrin, hematoporphyrin and methylene blue which have been shown to locate in endosomes and lysosomes of cells in culture. This is in most cases due to endocytic uptake of the photosensitizer. Thus, the photosensitizing agent is preferably an agent which is taken up into the internal compartments of lysosomes or endosomes. Preferably the photosensitizing agent is taken up into intracellular compartments by endocytosis. Further appropriate photosensitizers for use in the invention are described in WO03/020309, which is also incorporated herein by reference, namely sulphonated meso-tetraphenyl chlorins, preferably $TPCS_{2a}$.

However, other photosensitizing agents which locate to other intracellular compartments for example the endoplasmic reticulum or the Golgi apparatus may also be used. It is also conceivable that mechanisms may be at work in which the effects of the photochemical treatment are on other components of the cell (i.e. components other than membrane-restricted compartments). Thus, for example one possibility may be that the photochemical treatment destroys molecules important for intracellular transport or vesicle fusion. Such molecules may not necessarily be located in membrane-restricted compartments, but the photochemical damage of such molecules may nevertheless lead to photochemical internalisation and/or enhanced activity of the kinase inhibitor, e.g. by a mechanism in which photochemical effects on such molecules leads to reduced transport of the kinase inhibitor to degradative vesicles such as lysosomes, so that the kinase inhibitor can escape to the cytosol before being degraded. Thus in a preferred alternative, photosensitizers for use in the invention do not localize to intracellular compartments of the cell on internalization.

Examples of molecules not necessarily located in membrane restricted compartments are several molecules of the microtubular transport system such as dynein and components of dynactin; and for example rab5, rab7, N-ethylmaleimde sensitive factor (NSF), soluble NSF attachment protein (SNAP) and so on.

Classes of suitable photosensitizing agents for use in the invention which may be mentioned thus include porphyrins, phthalocyanines, purpurins, chlorins, benzoporphyrins, lysomotropic weak bases, naphthalocyanines, cationic dyes and tetracyclines and/or derivatives thereof (Berg et al., J. Photochemistry and Photobiology, 1997, 65, 403-409). Other suitable photosensitizing agents include texaphyrins, pheophorbides, porphycenes, bacteriochlorins, ketochlorins, hematoporphyrin or derivatives thereof, and derivatives thereof, endogenous photosensitizers induced by 5-aminolevulinic acid and derivatives thereof, Photofrin, dimers or other conjugates between photosensitizers.

Preferred photosensitizing agents include $TPPS_4$ (meso-tetraphenylporphine tetrasulfonate), $TPPS_{2a}$ (tetraphenylporphine disulfonate), $AlPcS_{2a}$ (aluminium phthalocyanine disulfonate), $TPCS_{2a}$ (tetraphenyl chlorin disulfonate) and $TPBS_{2a}$ (tetraphenyl bacteriochlorin disulfonate), and amphiphilic photosensitizers such as amphiphilic phthalocyanines, porphyrins and/or chlorins or pharmaceutically acceptable salts thereof. Other suitable photosensitizing agents include the compound 5-aminolevulinic acid or esters of 5-aminolevulinic acids or pharmaceutically acceptable salts thereof. Particularly preferred photosensitizing agents include $TPCS_{2a}$, $AlPcS_{2a}$ and $TPBS_{2a}$.

Further preferred photosensitizing agents are those which are not substrates for the ATP-binding cassette protein ABCG2 (breast cancer resistance protein), insofar as the photosensitizing agent is not transported out of cells by ABCG2 to any significant effect. See in this regard Robey et al., (2005, Cancer Biol. Ther., 4, p187-194) which describes ABCG2-mediated transport of photosensitizers and its effect on PDT. $TPPS_4$, $TPPS_{2a}$, $AlPcS_{2a}$, $TPCS_{2a}$ and $TPBS_{2a}$ are not substrates for the ABCG2 protein and are thus preferred. Photosensitisers which are not substrates for ABCG2 are preferably taken up by endocytosis. Without wishing to be bound by theory, when the photosensitisers are taken up by endocytosis they are located on the inside of the endosomal membrane and do not come into contact with the ABCG2 protein, which is located in the plasma membrane. Amphiphilic photosensitisers are also not likely to be substrates for the ABCG2 protein.

Particularly preferred photosensitizing agents are those which can be excited (i.e. absorb light) at wavelengths greater than 600 nm, and particularly preferably >630 nm. Examples of such photosensitizers include chlorins, phthalocyanines and bacteriochlorins.

Kinase inhibitors are molecules which inhibit the activity of the target kinase completely or partially. Thus said inhibitor inhibits the target kinase's activity, as assessed by its ability to phosphorylate at least one of its substrates, by at least 20%, preferably at least 30, 40, 50, 60, 70, 80 or 90%. Such tests of inhibition are conveniently carried out in vitro using an endogenous kinase and substrate to which the test inhibitor is added.

Inhibitors may act directly on the kinase domain of the inhibitor or may act indirectly to affect kinase activity, e.g. by affecting ligand binding and activation such as for example by binding to the extracellular domain of a receptor kinase. Preferred inhibitors are however those that act directly on the tyrosine kinase domain thereby affecting its activity (e.g. antagonists of kinase activity) and/or inhibitors that act intracellularly.

Kinase inhibitors may be antibodies, but in such cases are preferably not antibodies which bind to the extracellular domain of kinase receptors, e.g. tyrosine kinase receptors (e.g. EGFR antibodies C225 and cetuximab). In a preferred embodiment, inhibitors for use in the invention are not antibodies.

Inhibitors may block ABCG2 to remove photosensitizer resistance, i.e. reverse loss of intracellular accumulation of photosensitizers due to transport by ABCG2. However, in a preferred aspect, inhibitors for use in the invention do not have this property. Lapatinib, Sunitinib, Imatinib, Gefitinib, Nilotinib, Erlotinib and Tyrphostin AG1478 are ABCG2 inhibitors.

Inhibitors according to the invention may localize into intracellular compartments, e.g. endosomes, on internalization into the cell. However, in a preferred aspect, inhibitors, particularly tyrosine kinase inhibitors according to the invention do not localize in such compartments.

Preferred tyrosine kinase inhibitors according to the invention are small molecule inhibitors that act directly on the kinase domain of the kinase.

Preferred inhibitors include lapatinib (tradename Tyrkeb), sunitinib (tradename Suvent), imatinib (tradename Gleevac or Gleevec), gefitinib (tradename Iressa), dasatinib, nilotinib (tradename Tasigna), erlotinib (tradename Tarceva), tyrphostin (AG1478), sorafenib and bosutinib or a pharmaceutically acceptable salt thereof. The structures of these TKIs are provided in FIG. 1. Particularly preferred inhibitors are erlotinib, nilotinib, imatinib, tyrphostin and bosutinib. Especially preferred inhibitors are erlotinib, nilotinib and imatinib.

In a particularly preferred aspect, TKIs for use in the invention are 4-anilinoquinazolines, preferably having a structure of formula I:

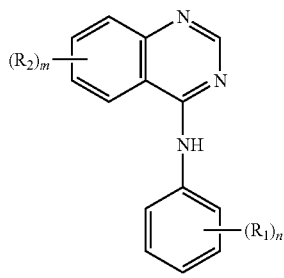

wherein, n and m are integers of 0, 1 or 2, preferably n=1 or 2 and m=2, $R_1$, each of which may be the same or different, is a halogen atom, preferably a Cl or F atom, or a —$C_2H$ group or an alkoxy group optionally substituted with an aryl group which may itself be substituted with one or more halogen atoms, $R_2$, each of which may be the same or different, is an alkoxy group optionally substituted with a heteroaromatic aryl group, or an optionally substituted furyl group, or a pharmaceutically acceptable salt thereof.

Preferably $R_1$ and/or $R_2$ are as provided in tyrphostin, lapatinib, gefitinib and/or erlotinib.

Tyrosine kinase inhibitors for use in the invention are preferably inhibitors of one or more receptor kinases, e.g. EGF, c-kit and PDGF-receptor kinases, or bcr-abl kinase. In one preferred aspect the inhibitor is not an inhibitor of the EGF receptor kinase.

Preferred serine/threonine kinase inhibitors for use in the invention are inhibitors of cyclin dependent kinases, Aurora kinase and mTOR kinase. Inhibitors of kinases in the MAP kinase pathway (i.e. in the cascade that involves Ras which activates RAF kinase, a serine/threonine-selective protein kinase, which activates MEK, another serine/threonine kinase, which activates mitogen-activated protein kinase (MAPK)). Particularly preferred examples of serine/threonine kinase inhibitors that may be used include Temsirolimus, Enzastaurin, Flavopirodol and CYC202 (whose structures are provided in FIG. 1).

Preferred pharmaceutically acceptable salts are acid addition salts with physiologically acceptable organic or inorganic acids. Suitable acids include, for example, hydrochloric, hydrobromic, sulphuric, phosphoric, acetic, lactic, citric, tartaric, succinic, maleic, fumaric, ascorbic and methanesulphonic acids. Preferred salts are mesylate salts. Procedures for salt formation are conventional in the art.

In a particularly preferred aspect, the photosensitizers are amphiphilic photosensitizers such as amphiphilic phthalocyanines, porphyrins and/or chlorins, in particular $TPPS_{2a}$, $TPBS_{2a}$, $AlPcS_{2a}$, $TPCS_{2a}$ or alternatively $TPPS_4$, especially preferably $TPPS_{2a}$ or $TPCS_{2a}$, or preferably $TPCS_{2a}$, $TPBS_{2a}$ or $AlPcS_{2a}$ (or pharmaceutically acceptable salts thereof). The inhibitors are TKIs of formula I indicated above, and/or selected from the list consisting of lapatinib, sunitinib, imatinib, gefitinib, dasatinib, nilotinib, erlotinib, tyrphostin, sorafenib and bosutinib. Particularly preferably the photosensitizer is $TPCS_{2a}$ and the TKI is imatinib, or the photosensitizer is $TPCS_4$ and the TKI is bosutinib. Further preferred combinations are any combination of the photosensitizers $TPCS_{2a}$, $TPBS_{2a}$ or $AlPcS_{2a}$ and the TKIs erlotinib, nilotinib or imatinib, e.g. imatinib, erlotinib, bosutinib or nilotinib and the photosensitizer $TPCS_{2a}$, or the photosensitizer $TPPS_{2a}$ and the TKI tyrphostin.

"Irradiation" of the cell to activate the photosensitizing agent refers to the administration of light directly or indirectly as described hereinafter. Thus cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells.

"Enhancing the activity of a kinase inhibitor" refers to increasing one or more of the inhibitor's activities to a measurable extent. This includes inhibition of the kinase's direct activity, i.e. phosphorylation (i.e. enhanced inhibitor activity is reflected by reduced phosphorylation of one or more of the kinase's substrates) or enhancing effects associated with the activity of the kinase inhibitor in a cell. The latter may include cell death, in which case cell death is enhanced. Enhanced activity may be qualitative or quantitative but is preferably the latter. Thus the inhibitor's activity may be improved 2, 3, 4, 5, 6, 7, 8, 9, 10, 20 fold or more relative to its activity without photochemical treatment. In relation to phosphorylation, enhanced activity may be reflected by a reduction in phosphorylation (when compared to a control experiment in which no inhibitor is added) of at least 10, 20, 30, 40, 50, 60, 70, 80 or 90% on one or more substrates of the kinase. Phosphorylation can be measured by Western blotting or any suitable alternative method. Cell death, may be increased 2, 3, 4, 5, 6, 7, 8, 9 or 10 fold or more, e.g. to viability levels below 80, 70, 60, 50, 40, 30, 20 or 10%.

Preferably the activity is enhanced to the extent that more than additive effects are observed relative to the combination of (i) the photochemical method alone without the kinase inhibitor and (ii) the kinase inhibitor alone without the photochemical method.

Thus in a preferred aspect, the present invention provides a method for enhancing the activity of a kinase inhibitor, preferably a tyrosine kinase inhibitor, comprising contacting a cell with said kinase inhibitor and a photosensitizing agent, and irradiating the cell with light of a wavelength effective to activate the photosensitizing agent, wherein the activity of the kinase inhibitor is enhanced more than the combined enhancement observed by (i) performing said method in the absence of said kinase inhibitor and (ii) performing said method in the absence of said photosensitizing agent and said irradiation step, i.e. synergy between these methods is observed.

"Synergy" as used to herein refers to a quantitative improvement over merely additive effects. In the methods of the invention, this refers to an improvement over the effects of the photochemical treatment and the kinase inhibitor effects merely added together.

Optionally, one or other or both of the photosensitizing agent and the kinase inhibitor may be attached to, or associated with, or conjugated to one or more carrier molecules or targeting molecules which can act to facilitate or increase the uptake of the photosensitizing agent or kinase inhibitor or can act to target or deliver these entities to a particular cell type, tissue or intracellular compartment.

Examples of carrier systems include polylysine or other polycations, dextran sulphate, different cationic lipids, liposomes, reconstituted LDL-particles or sterically stabilised liposomes. These carrier systems can generally improve the pharmacokinetics and increase the cellular uptake of the kinase inhibitor and/or the photosensitizing agent and may also direct the kinase inhibitor and/or the photosensitizing agent to intracellular compartments that are especially beneficial for obtaining photochemical internalisation, but they do not generally have the ability to target the kinase inhibitor and/or the photosensitizing agent to specific cells (e.g. cancer cells) or tissues. However, to achieve such specific or selective targetting the carrier molecule, the kinase inhibitor and/or the photosensitizer may be associated or conjugated to specific targetting molecules that will promote the specific cellular uptake of the kinase inhibitor into desired cells or tissues. Such targetting molecules may also direct the kinase inhibitor to intracellular compartments that are especially beneficial for obtaining photochemical internalization.

Many different targeting molecules can be employed, e.g. as described in Curiel (1999), Ann. New York Acad. Sci. 886, 158-171; Bilbao et al., (1998), in Gene Therapy of Cancer (Walden et al., eds., Plenum Press, New York); Peng and Russell (1999), Curr. Opin. Biotechnol. 10, 454-457; Wickham (2000), Gene Ther. 7, 110-114.

The carrier molecule and/or the targetting molecule may be associated, bound or conjugated to the kinase inhibitor, to the photosensitizing agent or both, and the same or different carrier or targetting molecules may be used. As mentioned above, more than one carrier and/or targetting molecule may be used simultaneously.

Preferred carriers for use in the present invention include polycations such as polylysine (e.g. poly-L-lysine or poly-D-lysine), polyethyleneimine or dendrimers (e.g. cationic dendrimers such as SuperFect7); cationic lipids such as DOTAP or Lipofectin and peptides.

The method of the invention may be put into practice as described below. In the method of the invention, the kinase inhibitor, e.g. TKI, together with a photosensitizing compound are applied simultaneously or in sequence to the cells, whereupon at least the photosensitizing compound, and in some cases also the kinase inhibitor, are endocytosed or in other ways translocated into endosomes, lysosomes or other intracellular membrane restricted compartments. Preferably the photosensitizing agent and the kinase inhibitor are provided separately. In a preferred embodiment the photosensitizing agent and the kinase inhibitor are not physically linked together, i.e. not attached to, associated with or conjugated to one another.

The kinase inhibitor and the photosensitizing compound may be applied to the cells together or sequentially. Conveniently, the kinase inhibitor is administered to the cell simultaneously with the photosensitizing compound. Alternatively, however, the kinase inhibitor and the photosensitizing compound can be administered sequentially. The kinase inhibitor and the photosensitizing compound may be taken up by the cell into the same or different intracellular compartments (e.g. they may be co-translocated), when a kinase inhibitor is used that is internalized in this way.

The cells are then exposed to light of suitable wavelengths to activate the photosensitizing compound which in turn leads to the disruption of the intracellular compartment membranes. In instances in which a kinase inhibitor has been used which has located into these compartments, disruption will lead to the release of the inhibitor into the cytosol. Thus, in these methods the final step of exposing the cells to light results in the kinase inhibitor being released from the same intracellular compartment as the photosensitizing agent and becoming present in the cytosol. It is however possible that activation of the photosensitizing agent has an additional or alternative result which enhances the kinase inhibitor's activity. Thus the invention is not limited to release of kinase inhibitors into the cytosol or enhanced levels of the inhibitors in the cytosol, though such a result forms a preferred aspect of the invention.

WO 02/44396 (which is incorporated herein by reference) described a method in which the order of the steps in the method may be changed such that for example the photosensitizing agent is contacted with the cells and activated by irradiation before the molecule to be internalised (and the carrier) are brought into contact with the cells. This adapted method takes advantage of the fact that it is not necessary for the molecule to be internalised to be present in the same cellular subcompartment as the photosensitizing agent at the time of irradiation.

Thus in one embodiment, said photosensitizing agent and said kinase inhibitor are applied to the cell together, or said photosensitizing agent is applied separately relative to said kinase inhibitor. As a consequence they may or may not be taken up by the cell into the same intracellular compartment and said irradiation may then be performed. This is referred to as a "light after" method.

In an alternative embodiment, said method can be performed by contacting said cell with a photosensitizing agent, contacting said cell with the kinase inhibitor to be introduced and irradiating said cell with light of a wavelength effective to activate the photosensitizing agent, wherein said irradiation is performed prior to the cellular uptake of said kinase inhibitor into an intracellular compartment containing said photosensitizing agent (e.g. it may be present in a different intracellular compartment at the time of light exposure), preferably prior to cellular uptake of said kinase inhibitor into any intracellular compartment, e.g. prior to any cellular uptake. This is the so-called "light before" method.

In a preferred aspect a "light after" method is used in which the kinase inhibitor is applied to the cells before activation of the photo sensitizer. Thus the kinase inhibitor may be applied before application and then activation of the photosensitizer or, alternatively, before, together with, or after the photosensitizer, but before irradiation to activate the photosensitizer.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with a photosensitizing agent and with the kinase inhibitor may be carried out in any convenient or desired way. Thus, if the contacting step is to be carried out in vitro the cells may conveniently be maintained in an aqueous medium, such as for example appropriate cell culture medium, and at the appropriate time point the photosensitizing agent and/or kinase inhibitor can simply be added to the medium under appropriate conditions, for example at an appropriate concentration and for an appropriate length of time. For example, the cells may be contacted with the kinase inhibitor in the presence of serum-free medium.

The comments below discuss the application of the photosensitizer and the kinase inhibitor to the cells separately. As discussed above however, these agents may be applied to cells together or sequentially and in the latter case either the photosensitizer, but preferably the kinase inhibitor, may be applied first.

The photosensitizing agent is brought into contact with the cells at an appropriate concentration and for an appropriate length of time which can easily be determined by a skilled person using routine techniques, and will depend on such factors as the particular photosensitizing agent used and the target cell type and location. The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted. As mentioned in the foregoing however, it has not been confirmed that the observed effects are reliant on disruption of intracellular compartments. However levels sufficient to achieve this effect may be used for convenience. For example photosensitizing agents as described herein may be used at a concentration of for example 10 to 50 μg/ml. For in vitro use the range can be much broader, e.g. 0.05-500 μg/ml. For in vivo human treatments the photosensitizing agent may be used in the range 0.05-20 mg/kg body weight when administered systemically or 0.1-20% in a solvent for topical application. In smaller animals the concentration range may be different and can be adjusted accordingly.

The time of incubation of the cells with the photosensitizing agent (i.e. the "contact" time) can vary from a few minutes to several hours, e.g. even up to 48 hours or longer, e.g. 12 to 20 hours. The time of incubation should be such that the photosensitizing agent is taken up by the appropriate cells, e.g. into intracellular compartments in said cells.

The kinase inhibitor is similarly brought into contact with the cells at an appropriate concentration and for an appropriate length of time. As mentioned above, it has been found that the contact may be initiated even several hours after the photosensitizing agent has been added and irradiation taken place.

Determining the appropriate doses of kinase inhibitor for use in the methods of the present invention is routine practice for a person skilled in the art. For in vitro applications an exemplary dose of a kinase inhibitor would be approximately 0.1 to 500 μg kinase inhibitor per ml and for in vivo applications approximately $10^{-6}$ to 1 g kinase inhibitor per injection in humans. For example, TKIs may be administered at levels of less than 50 μM, e.g. less than 30 μM, for example 5 to 30 μM, especially preferably less than 10 μM, for example from 0.1 to 1 μM, where the concentration indicated reflects the levels in contact with the cell. By way of example, erlotinib is typically given in doses of 100-150 mg per day per patient. Imatinib is typically given in doses of 400-800 mg per patient per day and nilotinib is typically given in two doses of 400 mg per day per patient. Typical blood concentrations of these inhibitors after incubation may be 1-10 μM for erlotinib, 1-4 μM for imatinib and 1-5 μM for nilotinib.

The above doses reflect normal therapeutic doses for kinase inhibitors. However the kinase inhibitor may be applied at a concentration which results in a lower dose than would normally be required for therapeutic purposes, due to the increased efficacy of the kinase inhibitors when used in the methods of the invention. For example, in a therapeutic use of the invention the kinase inhibitor may be applied at less than a therapeutically effective amount. Thus in a preferred embodiment of the present invention doses 20, 30, 40, 50, 60, 70, 80, 90, 95, 96, 97, 98 or 99% less than these doses may be used. Alternatively expressed, as little as 1% of a normal therapeutic dose may be used, e.g. less than 50, 40, 30, 20, 10, 5, 4, 3, 2 or 1% of a normal therapeutic dose. As referred to herein a therapeutic dose is one which achieves the desired effect (e.g. therapeutically beneficial cell death) when used alone, i.e. without photochemical treatment.

In an alternative aspect of the invention the kinase inhibitor may be given initially as a single high dose in combination with PCI e.g. more than double the normal therapeutic dose (disclosed above), e.g. at least 2-5 times a normal therapeutic dose.

An appropriate concentration can be determined depending on the efficiency of uptake of the kinase inhibitor in question into the cells in question and the final concentration it is desired to achieve in the cells. Thus "transfection time" or "cellular uptake time" i.e. the time for which the kinase inhibitors are in contact with the cells can be a few minutes or up to a few hours, for example a transfection time of from 10 minutes until up to 24 hours, for example 30 minutes up to 10 hours or for example 30 minutes until up to 2 hours or 6 hours can be used. Longer incubation times may also be used, e.g. 24 to 96 hours or longer, e.g. 5-10 days.

An increased transfection time usually results in increased uptake of the molecule in question, i.e. the photosensitizer and/or the kinase inhibitor. However, shorter incubation times, for example 30 minutes to 1 hour, can also result in an improved specificity of uptake. Thus, in selecting a transfection time for any method, an appropriate balance must be struck between obtaining a sufficient uptake of the photosensitizer and/or kinase inhibitor while maintaining sufficient specificity of the PCI treatment.

The incubation of the cells with the photosensitizing agent and/or the kinase inhibitor may optionally be followed by a period of incubation with photosensitizer and/or kinase inhibitor-free medium before the cells are exposed to light or the kinase inhibitor or photosensitizer is added, e.g. for 10 minutes to 8 hours, especially 1 to 4 hours.

In vivo an appropriate method and time of incubation by which the kinase inhibitor and photosensitizing agents are brought into contact with the target cells will be dependent on factors such as the mode of administration and the type of kinase inhibitor and photosensitizing agents. For example, if the kinase inhibitor is injected into a tumour, tissue or organ which is to be treated, the cells near the injection point will come into contact with and hence tend to take up the kinase inhibitor more rapidly than the cells located at a greater distance from the injection point, which are likely to come into contact with the kinase inhibitor at a later time point and lower concentration.

In addition, a kinase inhibitor administered by intravenous injection or orally may take some time to arrive at the target cells and it may thus take longer post-administration e.g. several days, in order for a sufficient or optimal amount of the kinase inhibitor to accumulate in a target cell or tissue. The same considerations of course apply to the time of administration required for the uptake of the photosensitizing agent into cells. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the kinase inhibitor has either been taken up, or will be taken up after sufficient contact with the target cells, into the cell, for example into the same or different intracellular compartments relative to the photosensitizing agent or (ii) after irradiation the kinase inhibitor is in contact with the cells for a period of time sufficient to allow its uptake into the cells. Conveniently the kinase inhibitor is taken up into intracellular compartments affected by activation of the photosensitizing agent (e.g. compartments in which the photosensitizing agent is present) and may be taken up before or after irradiation.

The light irradiation step to activate the photosensitizing agent may take place according to techniques and procedures well known in the art. For example, the wavelength and intensity of the light may be selected according to the photosensitizing agent used. Suitable light sources are well known in the art.

The time for which the cells are exposed to light in the methods of the present invention may vary. The efficiency of enhancing the activity of a kinase inhibitor increases with increased exposure to light to a maximum beyond which cell damage and hence cell death increases.

A preferred length of time for the irradiation step depends on factors such as the target, the photosensitizer, the amount of the photosensitizer accumulated in the target cells or tissue, the overlap between the absorption spectrum of the photosensitizer and the emission spectrum of the light source and the amount of cell death which can be tolerated or is desirable. Generally, the length of time for the irradiation step is in the order of minutes to several hours, e.g. preferably up to 60 minutes e.g. from 0.5 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes.

Appropriate light doses can be selected by a person skilled in the art and again will depend on the photosensitizer and the amount of photosensitizer accumulated in the target cells or tissues. For example, the light doses typically used for photodynamic treatment of cancers with the photosensitizer Photofrin and the protoporphyrin precursor 5-aminolevulinic acid is in the range 50-150 J/cm$^2$ at a fluence range of less than 200 mW/cm$^2$ in order to avoid hyperthermia. The light doses are usually lower when photosensitizers with higher extinction coefficients in the red area of the visible spectrum are used. However, for treatment of non-cancerous tissues with less photosensitizer accumulated the total amount of light needed may be substantially higher than for treatment of cancers. Furthermore, if cell viability is to be maintained, the generation of excessive levels of toxic species is to be avoided and the relevant parameters may be adjusted accordingly.

The methods of the invention may inevitably give rise to some cell killing by virtue of the photochemical treatment i.e. through the generation of toxic species on activation of the photosensitizing agent. Depending on the proposed use, this cell death may not be of consequence and may indeed be advantageous for some applications (e.g. cancer treatment). The methods of the invention may be modified such that the fraction or proportion of the surviving cells is regulated by selecting the light dose in relation to the concentration of the photosensitizing agent. Again, such techniques are known in the art.

In applications in which cell death is desirable, substantially all of the cells, or a significant majority (e.g. at least 50%, more preferably at least 60, 70, 80 or 90% of the cells) are killed. This may be achieved through a combination of PDT effects (i.e. use of lethal doses of photosensitizer and/or irradiation) and the effects of the kinase inhibitor, or through enhancing the lethal effects of the kinase inhibitor through the method of the invention, in which case a PCI-type method occurs in which the internalized molecule, in this case the kinase inhibitor is the means by which cell death is achieved. This is a preferred aspect of the invention. In the former case, PDT (i.e. the method if performed without the kinase inhibitor) may contribute to cell death to the extent that at least 10, 20, 30, 40, 50, 60, 70, 80, 90 or 95% of cells are killed by this treatment alone. The extent of mortality would then be increased by use of the kinase inhibitor in the method.

In applications in which viable cells are desirable, substantially all of the cells, or a significant majority (e.g. at least 50%, more preferably at least 60, 70, 80 or 90% of the cells) are not killed.

Regardless of the amount of cell death induced by the activation of the photosensitizer, for the kinase inhibitor to have an effect in the cells, it is important that the light dose is regulated such that some of the individual cells wherein the PCI effect is manifested are not killed by the photochemical treatment alone (although they may subsequently be killed by the kinase inhibitor). In a preferred aspect of the invention the light dose is such that a PCI effect is achieved in that substantial cell death is not Obtained in the absence of the kinase inhibitor. Thus preferably, in methods of the invention the photochemical treatment, if used alone, would retain viable cells to the extent indicated above, i.e. at least 50%, more preferably at least 60, 70, 80, 90, 95, 96, 97, 98 or 99% remain viable, i.e. is not a method of PDT (PDT in this context is considered to kill at least 10%, but preferably at least 20 or 30% or more of cells as defined above). In cases where cell death is desirable the majority or predominant cell death would then be due to the action of the kinase inhibitor and not a PDT effect. A PCI method makes it possible for the kinase inhibitor to penetrate deeper into the tissue than penetration which is possible with PDT. Also, it is advantageous for cell death to occur as a result of the action of the kinase inhibitor rather than PDT as in many cases the kinase inhibitor improves selectivity for cancer cells over neighbouring normal cells.

To achieve PCI rather than PDT effects, the parameters of the method may be modified accordingly as discussed above. Thus the photosensitizer dose and/or light dose or irradiation time may be adjusted accordingly. For example as little as 10% of a light dose that would result in PDT may be used. Typical PDT light doses are mentioned above.

Cytotoxic effects may be achieved by using for example a kinase inhibitor, such as a TKI, which is internalized into a tumour cell by the method of the invention e.g. to cause death of the tumour cell.

The methods of the invention may be used in vitro, ex vivo or in vivo, e.g. for therapeutic purposes.

The methods of the invention may also be used in treating any disease which benefits from the action of kinase inhibitors or in which kinase activity suppression is beneficial, e.g. in which aberrant or abnormal levels of kinase activity are present, for example in cancer patients. Other diseases that may be treated using the methods of the invention include autoimmune and inflammatory diseases, for example arthritis, and conditions of aberrant angiogenesis, for example age-related macular degeneration. Preferably, non-ocular diseases are treated.

Preferred patients are the source of cells as described herein, i.e. preferably mammalian, especially preferably human.

Preferred cancers are those which are accessible for irradiation and typically include cancer appearing on internal or external body surfaces, such as the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumours in solid tissues that can be made accessible to photoactivating light. e.g. either directly, at time of surgery, or via an optical fibre inserted through a needle.

Preferred cancers are thus head, neck, ovarian, skin, breast, lung, pancreatic, prostate, oesophageal, cervical, colorectal, sarcoma, stomach bladder and brain cancers, including different sub-types of such cancers and different stages thereof, such as stage 0, I, II, III or IV. In a preferred aspect, methods of the invention may be used to treat drug-resistant cancers.

Thus in a preferred aspect the present invention provides a method of treating or preventing a disease, disorder or infection in a patient by enhancing kinase inhibitor activity, comprising the steps of contacting one or more cells of said patient with a kinase inhibitor, e.g. a TKI, and a photosensitizing agent, and irradiating said cells with light of a wavelength effective to activate the photosensitizing agent.

Thus, the invention further provides a method of treatment of a patient as described herein before comprising administering to said patient compositions of the present invention (as described hereinafter), i.e. a method comprising the steps of introducing a kinase inhibitor into a cell as described hereinbefore. Preferably said methods are used to treat cancer.

In vivo, any mode of administration common or standard in the art may be used, e.g. injection, infusion, topical or oral administration, both to internal and external body surfaces etc. For in vivo use, the invention can be used in relation to any tissue which contains cells to which the photosensitizing agent and the kinase inhibitor are localized, including body fluid locations, as well as solid tissues. All tissues can be treated as long as the photosensitizer is taken up by the target cells, and the light can be properly delivered.

Alternatively described, the present invention provides the use of a kinase inhibitor and/or a photosensitising agent as described herein in the preparation of a medicament for treating or preventing a disease, disorder or infection by enhancing kinase inhibitor activity in a patient. In a further alternative, the present invention provides a kinase inhibitor and/or a photosensitising agent as described herein for treating or preventing a disease, disorder or infection by enhancing kinase inhibitor activity in a patient. Preferably, the treatment/prevention is performed as described herein.

Said disease, disorder or infection is preferably typified by enhanced kinase activity or in which suppression of kinase activity (e.g. EGFR) would be beneficial. Preferably said medicament is for cancer therapy, i.e. for treating tumour cells, or for treating autoimmune or inflammatory diseases, for example arthritis, or conditions of aberrant angiogenesis, for example age-related macular degeneration, or other diseases which would benefit from enhanced kinase inhibitor, e.g. TKI activity.

As defined herein "treatment" refers to reducing, alleviating or eliminating one or more symptoms of the disease, disorder or infection which is being treated, relative to the symptoms prior to treatment. "Prevention" refers to delaying or preventing the onset of the symptoms of the disease, disorder or infection.

According to the different embodiments set out above, the said photosensitizing agent and said kinase inhibitor are contacted with cells or tissues of a patient simultaneously or sequentially and said cells are irradiated with light of a wavelength effective to activate the photosensitizing agent and irradiation is performed prior to, during or after the cellular uptake of said kinase inhibitor into the cell e.g. into an intracellular compartment containing said photosensitizing agent, preferably prior to cellular uptake of said transfer molecule into any intracellular compartment.

In a further aspect, the invention provides a composition containing a kinase inhibitor and a photosensitizing agent, which may be provided separately, as described herein. In a further aspect the invention provides said composition for use in therapy.

A yet further aspect of the invention provides a cell or a population of cells containing a kinase inhibitor which has been introduced into said cell, which cell is obtainable by a method of the present invention.

The present invention also provides a kit (or product) comprising a kinase inhibitor and a photosensitizing agent as described herein for separate, simultaneous or sequential use, preferably for the therapeutic uses described herein.

Compositions of the invention may be formulated in any convenient manner according to techniques and procedures known in the pharmaceutical art, e.g. using one or more pharmaceutically acceptable carrier or excipients. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc. In connection with the photosensitizing agent the potency/ability to disrupt membranes on irradiation and/or achieve cell death, should also be taken into account.

Figure 2:
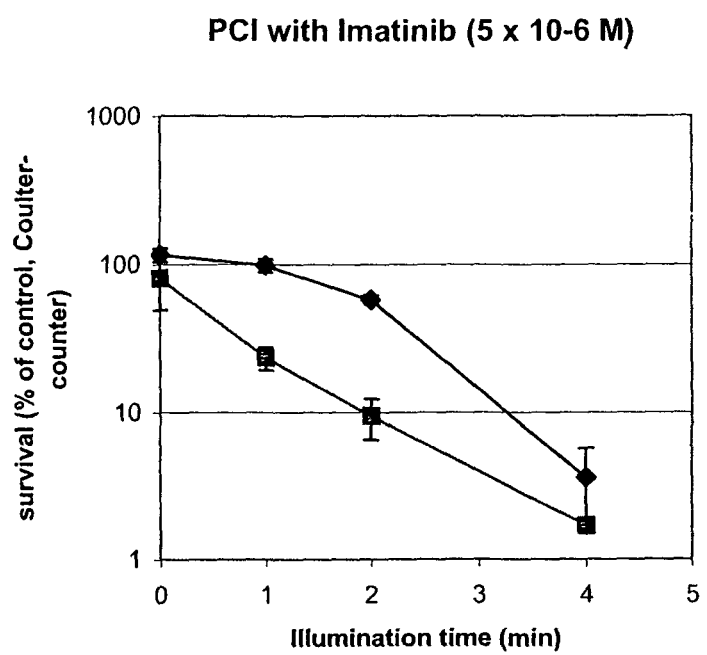
Figure 3:
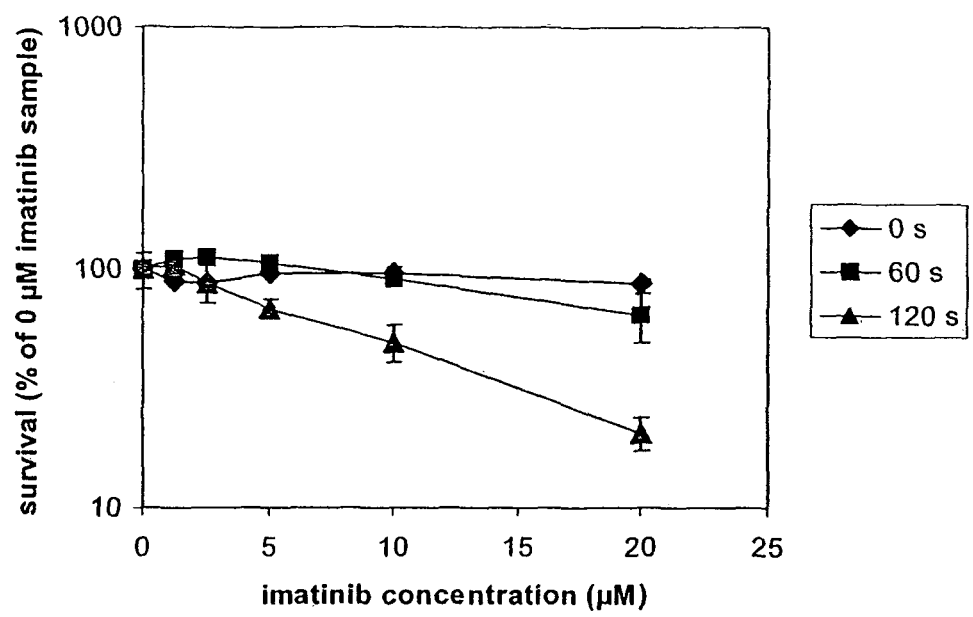
Figure 4:
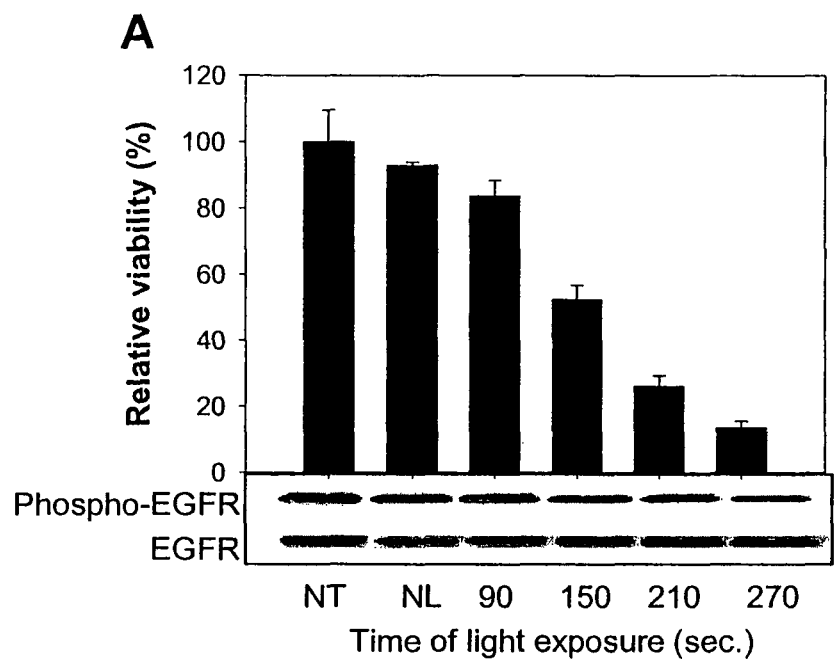
Figure 5:
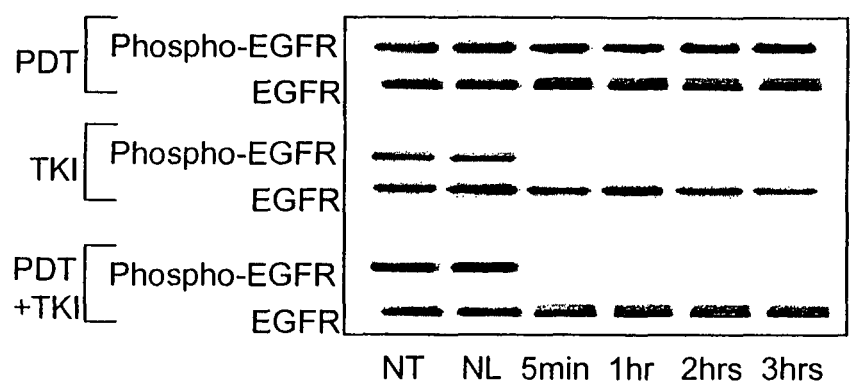
Figure 6:
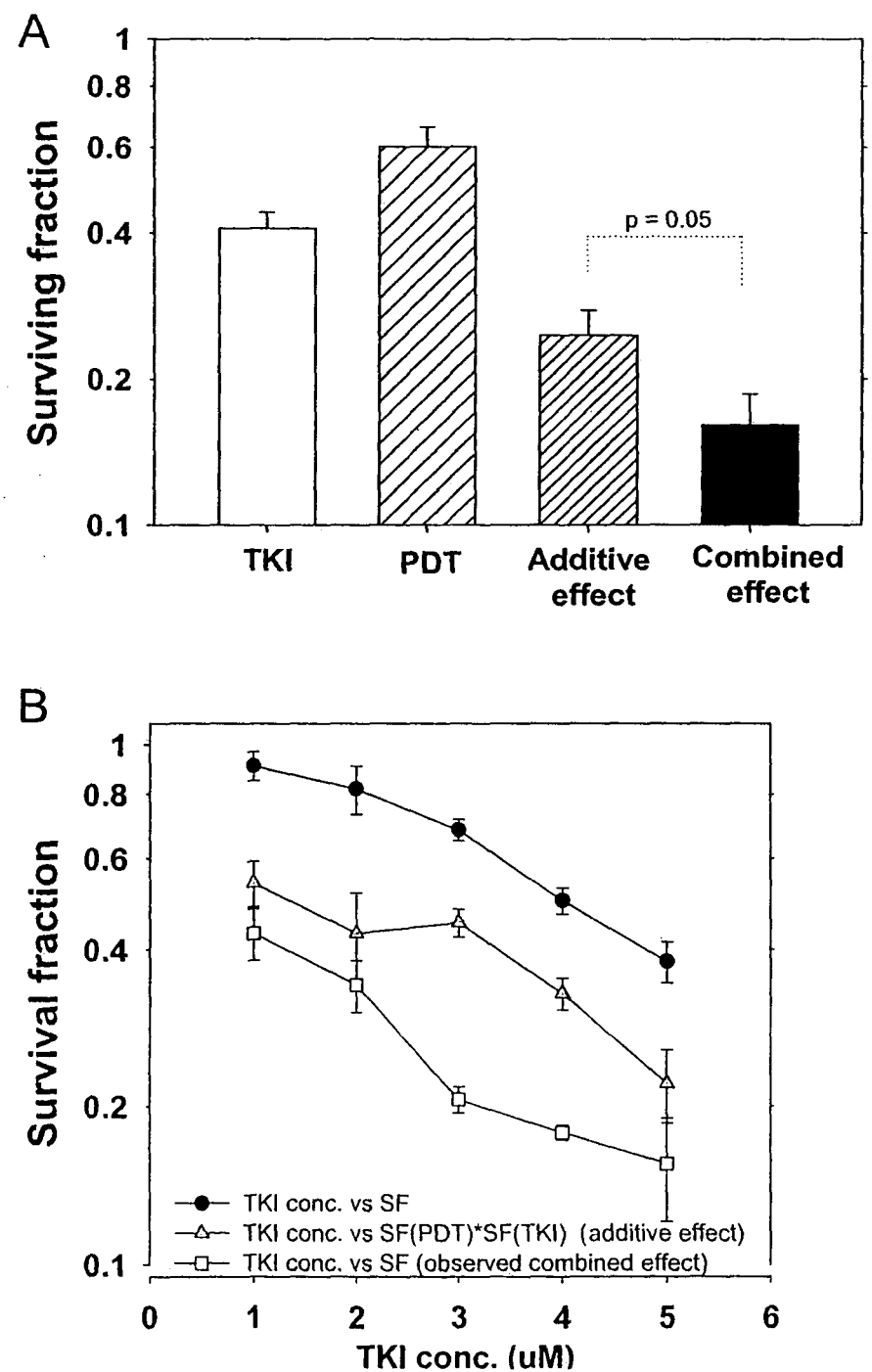

The invention will now be described in more detail in the following non-limiting Examples with reference to the following drawings in which:

FIG. 1 provides the structural formulae of kinase inhibitors mentioned herein,

FIG. 2 shows cell survival as a function of illumination time. The curve with diamonds represents cells that were treated with photosensitizer, but that did not receive imatinib. The curve with squares represents cells that were treated in the same way as those represented by diamonds but, in addition, received $5 \times 10^{-6}$ M imatinib, FIG. 3 shows cytotoxicity as a function of imatinib concentration for photochemical treatment after 0, 60 or 120 s illumination, FIG. 4 shows Western blots showing dose dependent photochemical effects on total and phosphorylated EGFR measured 1 hour after PDT in A-431 cells. The columns show cell viability after PDT treatment. Error bars are the mean+/−SE of triplicates, "NT" denotes no treatment and "NL" denotes no light, i.e. the cells have received photosensitizer but have not been illuminated, FIG. 5 shows Western blots showing time dependent effects on total and phosphorylated EGFR after PDT~$LD_{50}$, AG1478 (TKI)~$LD_{50}$ and the combination treatment in A-431 cells, and FIG. 6 shows the surviving fractions (SF) of A-431 cells after treatment with PDT, TKI (AG 1478) and the combination. The calculated additive effects of the 2 treatments are also shown. (A) shows the combined surviving fractions when 4 and 5 µM TKI was used, (B) shows the TKI concentration dependent calculated additive- and observed synergistic effects of the combination treatment. The data are the mean of three independent experiments. Error bars=SE.

Figure 7:
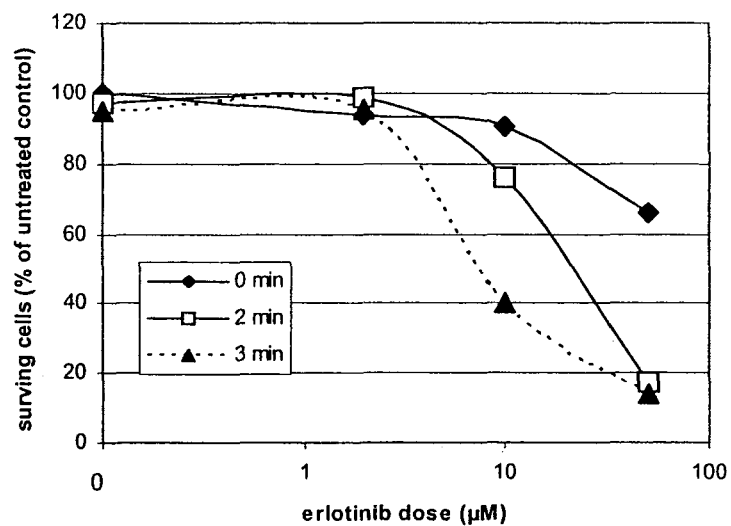
Figure 7:
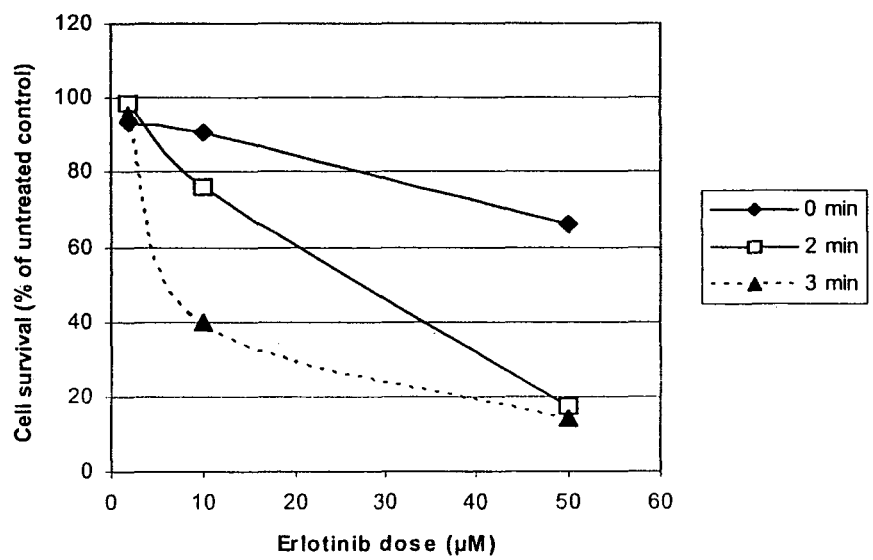

FIG. 7 shows the effect of PCI on the cytotoxicity of erlotinib in the NCI-H460 cell line. In Panel A the full range of doses tested is shown in a logarithmic scale, while in panel B a subgroup of the data is shown in a linear scale. The curves in panel B were used to estimate the erlotinib dose needed to obtain 30% cell killing (see text).

Figure 8:
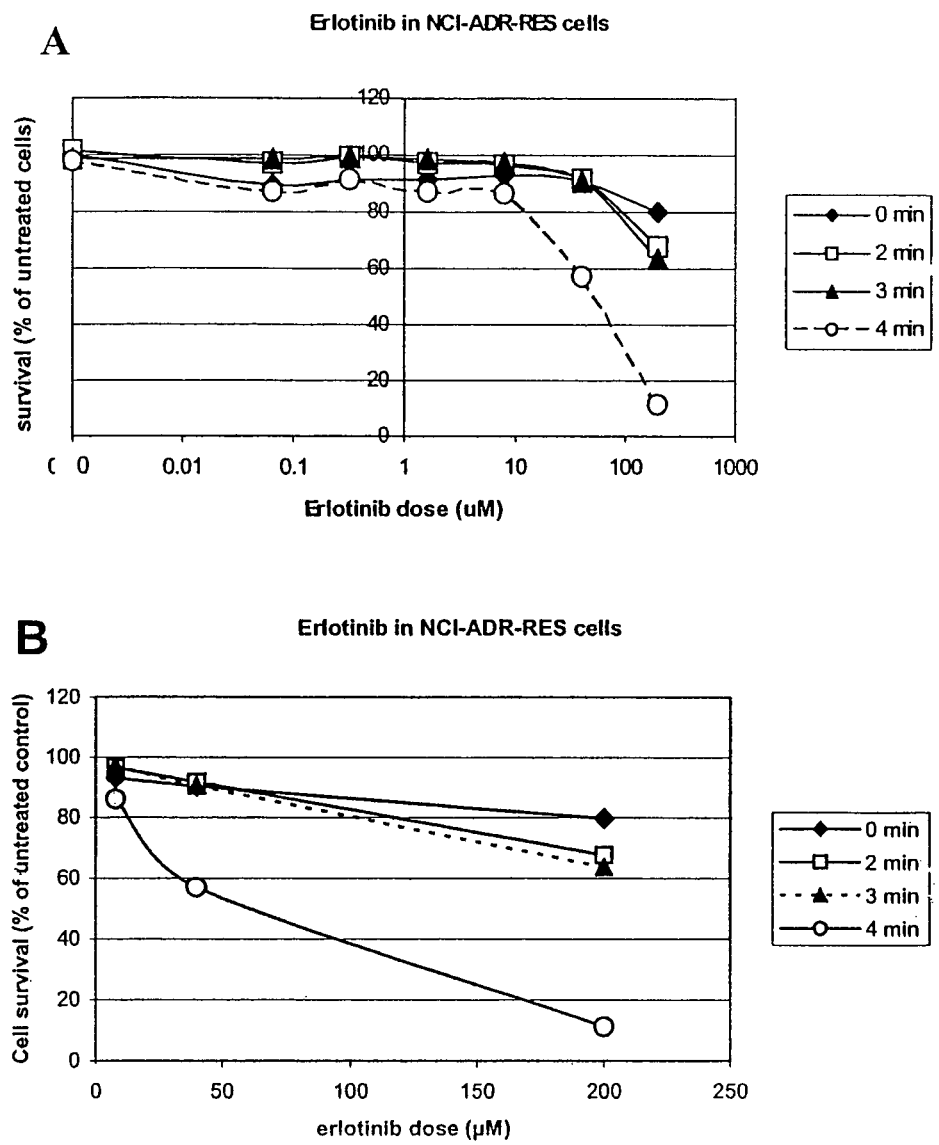

FIG. 8 shows the effect of PCI on the cytotoxicity of erlotinib in the NCI-ADR-RES cell line. In Panel A the full range of doses tested is shown in a logarithmic scale, while in panel B a subgroup of the data is shown in a linear scale. The curves in panel B were used to estimate the erlotinib dose needed to obtain 20% cell killing (see text).

Figure 9:
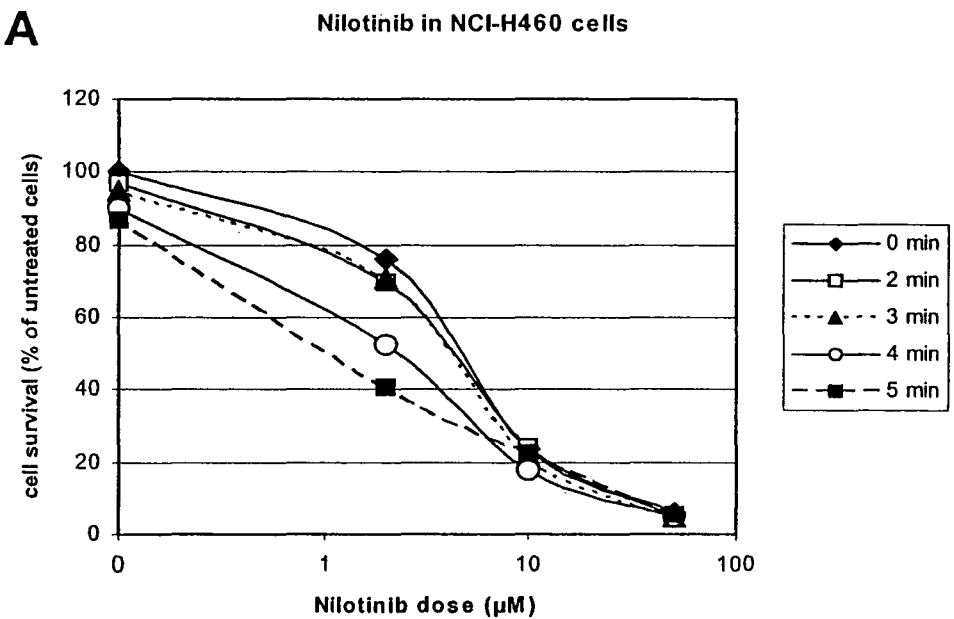
Figure 9:
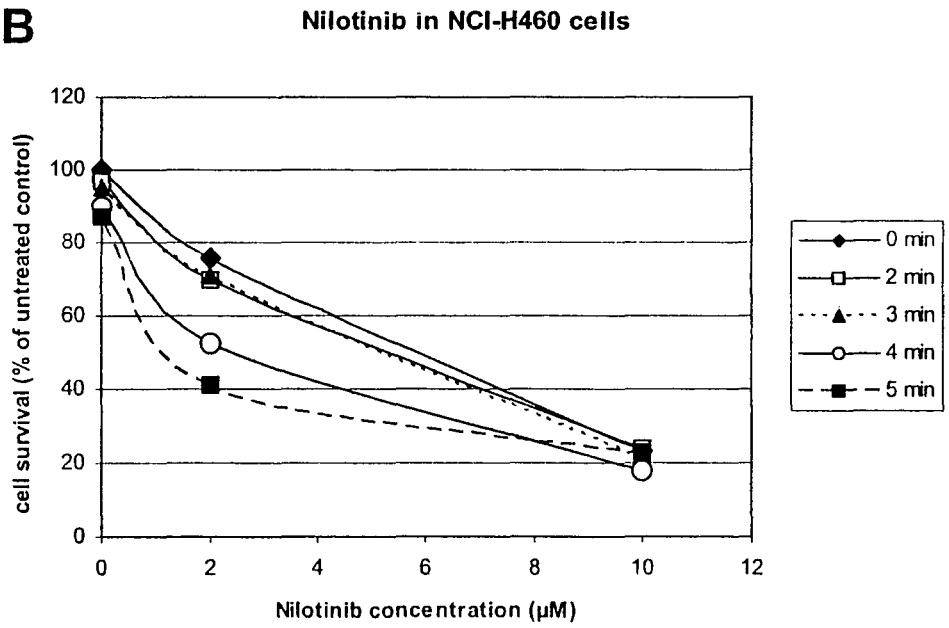

FIG. 9 shows the effect of PCI on the cytotoxicity of nilotinib in the NCI-H460 cell line. In Panel A the full range of doses tested is shown in a logarithmic scale, while in panel B a subgroup of the data is shown in a linear scale. The curves in panel B were used to estimate the nilotinib dose needed to obtain 50% cell killing (see text).

Figure 10:
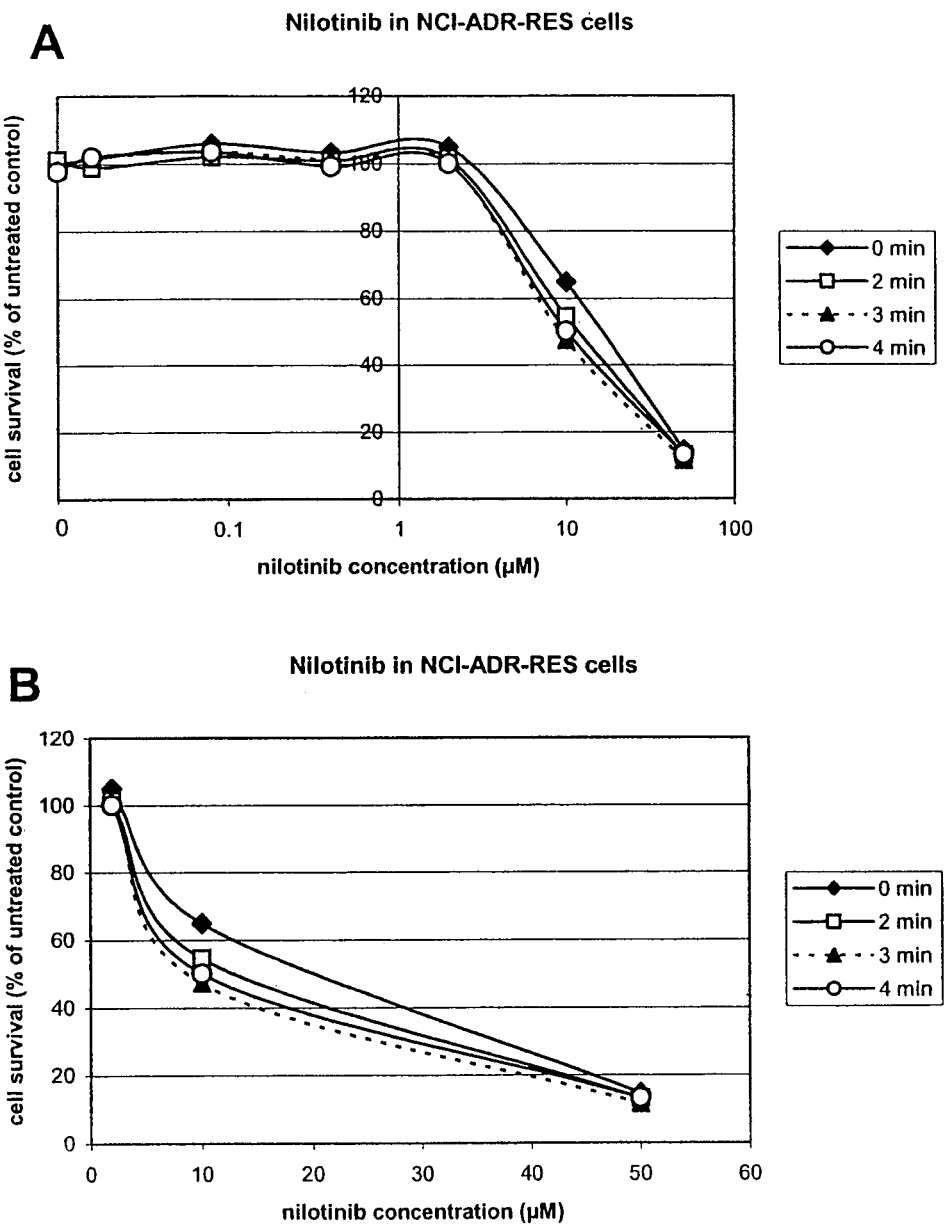

FIG. 10 shows the effect of PCI on the cytotoxicity of nilotinib in the NCI-ADR-RES cell line. In Panel A the full range of doses tested is shown in a logarithmic scale, while in panel B a subgroup of the data is shown in a linear scale. The curves in panel B were used to estimate the nilotinib dose needed to obtain 50% cell killing (see text).

EXAMPLES

Example 1

Methods

Cells from the A431 human epithelial carcinoma cell line (75,000 cells/well, 1.5 mL/well) were seeded into 6-well plates (Nunc, Denmark), incubated for 5 hours, then 0.1 µg/mL $TPCS_{2a}$ was added and the cells were further incubated for 18 h (5% v/v $CO_2$, 37° C. in DMEM medium with penicillin 100 U/mL, Glutamine 2 mM, Streptomycin 100 µg/mL). The cells were washed twice with medium (1 mL/well), incubated for 4 hours (37° C., 5% v/v $CO_2$) in serum-containing medium and illuminated for 1, 2 or 4 minutes as shown in FIG. 2. Imatinib mesylate was added directly to each well to a final concentration of $5 \times 10^{-6}$ M. After a further 72 hour incubation, cell survival was measured by Coulter Counter.

Coulter Counter Cell Count.

The cells were washed twice with Trypsin EDTA (200 µL/well) and incubated for 5 minutes (400 µL/well), then 1.5 mL medium was added and the mixture transferred to 10 mL tubes and centrifuged for 3 minutes at 1000 rpm. After removing the medium, 1 mL PBS (Phosphate Buffered Saline) was added and the solution mixed thoroughly. 750 µL was transferred to a beaker with 20 mL PBS and the amount of viable cells was determined with a Coulter Counter apparatus.

Results

The results are shown in FIG. 2. The value at zero illumination time for PCI+imatinib (i.e. the curve with squares) shows the effect of imatinib without illumination. It will be noted that imatinib, at the concentration used, had no significant effect on cell survival. The curve with diamonds shows the effect of illumination alone in $TPCS_{2a}$-treated cells. It can be seen that as expected cell survival decreases with increasing illumination time in a dose-dependent manner, i.e. providing a PDT effect. The curve with imatinib shows that illumination substantially increases the toxicity of imatinib. While the addition of imatinib has nearly no effect without illumination, illuminating imatinib-treated cells gives a substantially higher cytotoxicity than that which is seen with photochemical treatment alone (curve with diamonds).

Example 2

Methods

A431 cells (2500 cells/well, 100 µL/well) were seeded into 96-well plates (Nunc, Denmark) and incubated for 5 hours, then 0.1 µg/mL $TPCS_{2a}$ was added and incubated for 18 h (5% v/v $CO_2$, 37° C., DMEM medium with penicillin 100 U/mL, Glutamine 2 mM, Streptomycin 100 µg/mL). The cells were washed twice with medium (100 µL/well), incubated for 4 hours (37° C., 5% v/v $CO_2$) in serum-containing medium, illuminated for 0, 60 or 120 s as shown in FIG. 3 and imatinib mesylate was added up to 25 µM. After a further 72 hours incubation, cell survival was measured by the MTT assay.

MTT assay

The MTT method is based on reduction of a water-soluble tetrazolium salt (MTT) to a purple, insoluble formazan product by mitochondrial dehydrogenases present in living, metabolically active cells. 100 µL medium containing 0.25 µg MTT was added to the cells, followed by 1 h and 30 min of incubation (37° C., 5% v/v $CO_2$). The resulting formazan crystals were dissolved by adding 100 µl DMSO (Sigma, Mo., USA) per well. The 96 well plate was read by a Multiscan EX micro plate reader (Labsystems, Finland) with a 570 nm band pass filter.

Results

FIG. 3 shows cytotoxicity as a function of imatinib concentration for different types of photochemical treatments (0, 60 and 120 s illumination). In the Figure the effect of photochemical treatment alone (e.g. as shown by the curve with diamonds in FIG. 2) is corrected for by setting the value for this treatment (i.e. 0 µM imatinib) to 100% for each light dose. The 0 s curve represents the cytotoxicity of imatinib alone, showing only modest cytotoxicity even at the highest dose. As can be seen from the curves of the illuminated samples, illumination increased the cytotoxic effect of imatinib in a light dose-dependent manner. Since the cytotoxic effect of the pure photochemical treatment has been removed from consideration by correction as described above, and imatinib alone has almost no effect, this clearly shows the synergistic nature of the effect.

Example 3

Tyrphostin AG1478 is a 4-anilinoquinazoline and has the same backbone structure as the clinically relevant TKIs; Erlotinib, Gefitinib and Lapatinib. The TKIs in this family of drugs are small, lipophilic and function as competitive antagonists for the ATP binding pocket of EGFR.

Methods

Cell Culture and Cultivation

The studies were performed using the EGFR positive cell line A-431 human skin carcinoma (ATCC, CRL 1555). The A-431 cells were subcultured two or three times a week in DMEM (Bio Whitaker Europe, Velviers, Belgium). Media were supplied with 10% fetal calf serum (FCS) (GIBCO BRL, Paisley, UK), 100 U/ml penicillin, 100 U/ml streptomycin (Sigma, St. Loice, MO) and 2 mM glutamine (Bio Whittaker, Velviers, Belgium). The cells were grown and incubated in 75 $cm^2$ flasks (Nunc, Roskilde, Denmark) at 37° C. in a humidified atmosphere containing 5% $CO_2$.

Photodynamic Therapy

A-431 cells were seeded out and left to fasten for 6 hrs, or longer as described for the different combination treatment regimes with Tyrphostin AG1478, before an 18 hour incubation with 0.1 ug/ml LumiTrans ($TPPS_{2a}$, meso-tetraphenylporphine with two sulfonate groups on adjacent phenyl rings) (PCI Biotech AS, Oslo, Norway). The cells were then washed twice with drug free medium and chased in new drug free medium for 4 hrs to wash the $TPPS_{2a}$ off the plasma membrane. Cells were then exposed to blue light from Lumi-Source (PCT Biotech AS) consisting of 4 light tubes delivering light with λ=375-400 nm, maximum at 435 nm and irradiance=13.5 $mW/cm^2$ at different doses as indicated in the figures.

Combination Therapy of PDT and Tyrphostin AG 1478 (TKI)

Growth inhibition measurements were carried out after incubation of the cells for 72 hrs with different concentrations of AG1478 directly after exposure to light. Cell counting was performed with an in-house made Coulter counter after trypsination and resuspension in PBS. Two parallels of each sample were made, and the experiments were reproduced twice at least.

Toxicity of PDT during the sample preparations was evaluated by the MTT assay. The experiments were reproduced at least twice.

Western Blotting Analysis

At indicated times after light exposure the cell-medium was removed and cells were incubated for 2 minutes with 100 ng/ml EGF. Cells were then placed on ice and the sample preparation was performed as described before (Weyergang et al., 2007, Biochem. Pharmacol., 74, p226-235). The same amount of lysed cells from each sample, as measured by the absorption of nucleic acids at 260 nm, was subjected to gel electrophoresis on 12% SDS/polyacrylamide gels and blotted to Hybond-P PVDF membranes (Amersham Biosciences, Amersham Place, UK). Immunodetection was carried out using antibodies from Cell Signal Technology (Cell Signalling Technology Beverly, Mass.); EGFR antibody (#2232), Phospho-EGFR antibody (#2236), Anti-mouse IgG, HRP-linked Antibody (#7076) Anti-rabbit IgG, HRP-linked Antibody (#7074). ECL Plus Western blotting Detection Reagents, STORM and Image Quant from GE Healthcare (GE Healthcare, Amersham Place, UK) was used to detect protein bands on the membrane.

Statistical Methods for Evaluation of the PDT-TKI Combination Therapy

For each experiment the survival fraction (SF) of cells was found by dividing the number of treated cells by the average number of untreated cells in the two parallels. The expected additive effect was computed as $SF_{add}=SF_{PDT} \times SF_{TKI}$ where $SF_{PDT}$ and $SF_{TKI}$ refers to the observed effect after PDT or TKI treatment alone. $SF_{add}$ was then compared to the observed effect of the combined treatment, $SF_{comb}$, using the synergy/antagonism value F $$F = \log SF_{add}/\log SF_{Comb} = \log SF_{TKI} + \log SF_{PDT} - \log SF_{corab}$$

Synergistic effects between PDT and TKI resulted in positive F values. Antagonistic effects would result in negative F values. Significant deviations of F from zero were established through t-tests.

Results

EGFR in A-431 Cells is Resistant to PDT

In A-431 cells PDT did not result in a pronounced reduction in phospho-EGFR. Phosphorylation of the EGF receptor was not reduced after PDT with doses that reduced the relative viability up to 10% of that in untreated cells (FIG. 4).

Tyrphostin AG1478 Completely Attenuates EGFR Phosphorylation in A-431 Cells

The time dependent effects on EGFR after PDT, AG1478 and the combination treatment were studied in A-431 cells. The light dose administrated in these experiments reduced the cell viability to approximately 50% of that in untreated cells as measured by the MTT-method (data not shown). No decrease in phosphorylated EGFR was observed 1-4 hrs after PDT with $LD_{50}$ (FIG. 5). Incubating A-431 cells with 4 μM of AG1478 resulted, however, in a strong attenuation of EGFR phosphorylation in the same time scale. Combination therapy of the A-431 cells with PDT and AG1478 resulted in the same decrease in EGFR phosphorylation as that observed with the AG1478 treatment alone (FIG. 5).

Synergistic Effects are Obtained by Combination Therapy of PDT and Tyrphostin AG1478 in A-431 Cells In the A-431 cell line the combination therapy with PDT and AG1478 resulted in a synergistic effect when TKI was administrated directly after light exposure (FIG. 6). The average survival fraction of three independent experiments was 0.41 after TKI treatment only, 0.61 after PDT treatment only and 0.16 when the two treatments were combined (FIG. 6). The calculated additive effect of the two treatments was 0.24 and the synergy/antagonism parameter F of the experiments was positive and statistically significant from 0. The synergistic effect between AG1478 and PDT in the A-431 cell line seemed stronger when 4 or 5 uM AG1478 was administrated compared to 1 and 2 uM (F=0.18±0.09 and 0.17±0.08, p=0.05, respectively, see FIG. 7). In the present statistical model, results are accepted as synergistic when the combined effect of AG1478 and PDT is greater than the calculated additive effect, i.e. when $$-\log SF_{(AG1478+PDT)} > -\log[SF_{(AG1478)} \times SF_{(PDT)}]$$

The two lower curves in FIG. 6 indicate that this was the case for values of AG1478 between 1 and 5 μM, however not significant for the lowest AG1478 concentrations. However, the difference of the survival fractions in the log plot does not change uniformly with TKI concentration. We therefore evaluated the mean and st. error of this difference $$F = \log SF_{(TKI)} + \log SF_{(PDT)} - \log SF_{(TKI+PDT)}$$

in this TKI concentration range and find F=0.15+0.05 giving t=3.18 with 24 degrees of freedom and p=0.005, which is significant.

Example 4

Methods

Cell Culture

The cells were maintained in vitro in RPMI 1640+10% heat inactivated Fetal Bovine Serum+2 mM L-glutamine (growth medium) at 37° C. in 5% $CO_2$ and humidified conditions. The cells were harvested, washed, re-suspended into growth medium and counted (Beckman-Coulter Vi-CELL XR). The cells were re-suspended into growth medium at $6 \times 10^4$ viable cells/ml and plated into the middle 288 wells of 384 well tissue culture plates in 25 µl/well aliquots (Corning CellBind; black-wall, clear bottom). 25 µl of growth medium was added to the remaining wells.

Photochemical Treatment $TPCS_{2a}$ was diluted into growth medium at 0.4 µg/ml (NCI-H460) or 0.8 µg/ml (NCI-ADR-RES) and 25 µl was added to each test well (final assay concentrations 0.2 µg/ml and 0.4 µg/ml, respectively). The plates were incubated overnight at 37° C., in 5% humidified $CO_2$. Erlotinib and nilotinib were prepared in DMSO vehicle as stock solutions of 2-10 mM. The compounds were serially diluted from the stock solutions into growth medium in concentrations appropriate for the assays.

The plates were washed 6 times with 50 µl wash buffer using an EMBLA 384-well plate washer. 35 µl per well of compound/vehicle dilutions were added to the plates which were incubated for 4 hours at 37° C. in 5% humidified $CO_2$. The cells were illuminated for the different periods indicated in FIGS. 1-4, using a LumiSource® illumination device (PCI Biotech AS, Oslo Norway). LumiSource® is delivered with a bank of 4 light tubes ($4 \times 18$ W Osram L 18/67, Blue) emitting mainly blue light with a peak wavelength of approximately 420 nm, with an irradiance of about 13.5 $mW/cm^2$.

The plates were washed as before. 50 µl of growth medium+antibiotics (Sigma, UK) was added to each test well, and the plates were incubated for 66 h. Step 1 of the wash cycle was performed on each plate. CellTiter-Blue® reagent (Promega) was defrosted (from −20° C. storage); 7 µl of CellTiter-Blue® reagent was added to the test wells. The plates were centrifuged for 1 minute at 500 rpm, shaken for 1 minute at 500 rpm then incubated at 37° C., 5% humidified $CO_2$.

Fluorescence Measurement

Fluorescence was measured using a FlexStation® $II^{384}$ plate reader (570, nm excitation wavelength, 600 nm emission wavelength, 590 nm cut-off) after 3 h. % cell survival in the samples was calculated as % fluorescence in the samples, setting the fluorescence in untreated cells (i.e. cell receiving $TPCS_{2a}$, but no compound and no illumination) as 100%.

Results

FIG. 7 shows the results with erlotinib in the NCI-H460 human lung cancer cell line. It can be seen that for illumination times (2 and 3 min) that in themselves did not affect cell survival (FIG. 7A; 0 µM erlotinib dose) the erlotinib dose needed to induce 30% cell killing was lowered from 43 µM (no illumination) through 14 µM (2 min illumination) to 4 µM (3 min illumination) (FIG. 7B). Thus, photochemical internalisation could induce a 10 times potentiation of the effect of erlotinib. This is a clearly synergistic effect, since these light treatments alone had no effect under these conditions.

FIG. 8 shows results with erlotinib in the multi-drug resistant NCI-ADR-RES cancer cell line. In this cell line without illumination even the highest dose of erlotinib employed (200 µM) did not reduce cell viability by more than 20%. Comparisons of dose-efficiency with the illuminated samples is therefore inaccurate, but it can be seen from FIG. 8B that with 2 and 3 min illumination 20% cell killing was achieved at about 100 µM erlotinib, while with 4 min illumination a dose of only about 10 µM erlotinib was sufficient to obtain this level of cell killing. Since neither of these light doses affected cell killing on their own (FIG. 8A; 0 µM erlotinib dose) the experiment indicates that PCI can potentiate the effect of erlotinib about 20 times in the NCI-ADR-RES cell line, and that this is a clear synergistic effect.

In FIG. 9 the effect of PCI on cell killing by nilotinib in NCI-H460 cells is shown. It can be seen that the cytotoxicity increased with increasing illumination time and that the nilotinib dose needed to achieve 50% cell killing was reduced from 6 µM at 0 min illumination to about 1.7 µM at 5 min illumination, thus representing about 3.5 times potentiation of the nilotinib effect.

In FIG. 10 the effect of PCI on cell killing by nilotinib in NCI-ADR-RES cells is shown. It can be seen that the cytotoxicity increased with increasing illumination time and that the nilotinib dose needed to achieve 50% cell killing was reduced from about 20 µM at 0 min illumination to about 10 µM at 4 min illumination, thus representing about 2 times potentiation of the nilotinib effect.

In summary these results show that PCI can significantly potentiate the cytotoxic effect of both the Tyrosine Kinase Inhibitors erlotinib and nilotinib. The potentiation effect was most prominent for erlotinib, with a 10 times potentiation observed in the lung cancer cell line NCI-H460 and at least a 20 times potentiation seen in the multi-drug resistant cell line NCI-ADR-RES. For nilotinib the corresponding potentiation factors were 3.5 and 2, respectively. In most experiments the PCI-induced potentiation was observed under conditions where the photochemical treatment in itself did not have any cytotoxic effect, indicating a strong synergistic effect. The fact that PCI gives strong enhancement also on drug resistant cells indicates that PCI can be used to treat also tumours that are drug resistant, something that may be very important in a clinical situation.

The invention claimed is:

1. A method for enhancing the activity of tyrosine kinase inhibitors in target cells, said method comprising:
   (a) contacting a cell with a photosensitizing agent,
   (b) irradiating said cell with light of a wavelength effective to activate the photosensitizing agent, and
   (c) contacting said cell with a tyrosine kinase inhibitor before, after, or during, or a combination thereof, said irradiating,
   wherein the photosensitizing agent is not a substrate for the ATP-binding cassette protein ABCG2, wherein the photosensitizing agent is a di- or tetra-sulfonated aluminium pthalocyanine, sulfonated tetraphenylporphine, sulfonated meso tetraphenyl chlorin or sulfonated tetraphenyl bacteriochlorin, and wherein said tyrosine kinase inhibitor is lapatinib, sunitinib, imatinib, gefitinib, dasatinib, nilotinib, erlotinib, tyrphostin (AG 1478), sorafenib or bosutinib or a pharmaceutically acceptable salt thereof.

2. The method of claim 1 wherein the activity of the tyrosine kinase inhibitor is enhanced more than the combined enhancement observed by (i) performing said method in the absence of said tyrosine kinase inhibitor and (ii) performing said method in the absence of said photosensitizing agent and said irradiation step.

3. The method of claim 1 for enhancing the effects of a tyrosine kinase inhibitor-based drug.

4. The method of claim 1 wherein the photosensitizing agent is $TPPS_4$, $TPPS_{2a}$, $AlPcS_{2a}$, $TPCS_{2a}$ or $TPBS_{2a}$ or a pharmaceutically acceptable salt thereof.

5. The method of claim 1 wherein the photosensitizing agent is $TPCS_{2a}$, $AlPcS_{2a}$ or $TPBS_{2a}$.

6. The method of claim 1 wherein the tyrosine kinase inhibitor is a molecule which acts directly on the tyrosine kinase domain of a receptor tyrosine kinase.

7. The method of claim 1 wherein the tyrosine kinase inhibitor is erlotinib, nilotinib or imatinib.

8. The method of claim 1 wherein the photosensitizer is $TPCS_{2a}$ and the tyrosine kinase inhibitor is imatinib, erlotinib, bosutinib or nilotinib.

9. The method of claim 1 wherein the photosensitizer is $TPPS_{2a}$ and the tyrosine kinase inhibitor is tyrphostin.

10. The method of claim 1 wherein the amount of tyrosine kinase inhibitor contacted with a cell is less than a therapeutically effective amount when used without photochemical treatment.

11. The method of claim 1 wherein the photosensitizing agent and/or tyrosine kinase inhibitor is conjugated to a carrier molecule.

12. The method of claim 11 wherein the carrier is selected from a polycation, dextran sulphate, a cationic lipid, a liposome, a reconstituted LDL-particle and a sterically stabilised liposome.

13. The method of claim 11 wherein the carrier is selected from polylysine, polyethyleneimine, dendrimer, DOTAP, Lipofectin and a peptide.

14. The method of claim 1 wherein the photosensitizing agent and tyrosine kinase inhibitor are provided separately.

15. The method of claim 1 wherein irradiation of the cell does not result in photodynamic therapy.

16. The method of claim 15 wherein when said method is performed in the absence of said tyrosine kinase inhibitor irradiation of the cell does not result in substantial cell death.

17. The method of claim 1 wherein the cell is a mammalian cell.

18. A method of treating a disease, disorder or infection in a patient by enhancing tyrosine kinase inhibitor activity, said method comprising:
  (a) contacting one or more cells of said patient with a photosensitizing agent,
  (b) irradiating said cells with light of a wavelength effective to activate the photosensitizing agent, and
  (c) contacting said cell with a tyrosine kinase inhibitor before, after, or during, or a combination thereof, said irradiating,
  wherein the photosensitizing agent is not a substrate for the ATP-binding cassette protein ABCG2, wherein the photosensitizing agent is a di- or tetra-sulfonated aluminium pthalocyanine, sulfonated tetraphenylporphine, sulfonated meso tetraphenyl chlorin or sulfonated tetraphenyl bacteriochlorin, and wherein said tyrosine kinase inhibitor is lapatinib, sunitinib, imatinib, gefitinib, dasatinib, nilotinib, erlotinib, tyrphostin (AG 1478), sorafenib or bosutinib or a pharmaceutically acceptable salt thereof.

19. The method of claim 18 wherein the disease, disorder or infection is one which benefits from the action of tyrosine kinase inhibitors.

20. The method of claim 19 wherein the disease, disorder or infection is an autoimmune disease, inflammatory disease, or a condition of aberrant angiogenesis.

21. The method of claim 19 wherein the disease is cancer.

22. The method of claim 1 wherein the tyrosine kinase inhibitor
  (a) is taken up into the target cells before irradiation,
  (b) is taken up into the target cells during irradiation, or
  (c) is taken up into the target cells after irradiation.

23. The method of claim 22 wherein the tyrosine kinase inhibitor is added to said cells immediately after irradiation.

24. The method of claim 22 wherein the tyrosine kinase inhibitor is added to said cells prior to irradiation.

25. The method of claim 18 wherein said tyrosine kinase inhibitor is erlotinib, nilotinib or imatinib.

26. The method of claim 18 wherein the photosensitizing agent is TPCS2a and the tyrosine kinase inhibitor is imatinib, erlotinib, bosutinib or nilotinib.

27. The method of claim 18 wherein the amount of tyrosine kinase inhibitor contacted with said cells is less than a therapeutically effective amount when used without photochemical treatment.

\* \* \* \* \*